United States Patent
Paul et al.

(10) Patent No.: US 12,239,753 B2
(45) Date of Patent: Mar. 4, 2025

(54) METHODS AND DEVICES FOR PORTABLE STERILIZATION AND CONTAINMENT OF REUSABLE URINARY CATHETERS

(71) Applicant: CathBuddy, Inc., Woodbury, NY (US)

(72) Inventors: Souvik Paul, Woodbury, NY (US); Daniel Wollin, Newton, MA (US)

(73) Assignee: CathBuddy, Inc., Woodbury, NY (US)

( * ) Notice: Subject to any disclaimer, the term of this patent is extended or adjusted under 35 U.S.C. 154(b) by 0 days.

(21) Appl. No.: 18/229,608

(22) Filed: Aug. 2, 2023

(65) Prior Publication Data

US 2023/0372562 A1    Nov. 23, 2023

Related U.S. Application Data

(63) Continuation of application No. 16/847,830, filed on Apr. 14, 2020, now abandoned, which is a
(Continued)

(51) Int. Cl.
*B32B 25/06* (2006.01)
*A61L 2/08* (2006.01)
(Continued)

(52) U.S. Cl.
CPC .............. *A61L 2/10* (2013.01); *A61L 2/085* (2013.01); *A61L 2/12* (2013.01); *A61L 2202/11* (2013.01);
(Continued)

(58) Field of Classification Search
CPC ............... A61L 2/10; A61L 2/202; A61L 2/26
(Continued)

(56) References Cited

U.S. PATENT DOCUMENTS 3,683,928 A   8/1972  Kuntz
4,391,368 A   7/1983  Washington, Jr.
(Continued)

FOREIGN PATENT DOCUMENTS

CN   2440517 Y    8/2001
CN   209715892 U  12/2019
(Continued)

OTHER PUBLICATIONS

Jul. 17, 2020—(WO) ISR & WO—App. No. PCT/US20/28733.
(Continued)

*Primary Examiner* — Monzer R Chorbaji
(74) *Attorney, Agent, or Firm* — Banner & Witcoff, Ltd.

(57) ABSTRACT

The invention relates to systems and/or apparatuses capable of sterilizing medical products, preferably reusable urinary catheters, or other products using radiation. The apparatus of the present invention can be efficiently configured and designed to provide sterilization of the surfaces of a medical device by emitting radiation in a range sufficient and effective to destroy contaminants including pathogens and microorganisms. According to one preferred embodiment, radiation emitting diodes are placed in an array such that radiation is emitted into the interior of the apparatus enclosing the medical device for sterilization. Preferably, the systems and/or apparatuses can repeatedly sterilize medical products (e.g., reusable urinary catheters) without damaging them.

17 Claims, 14 Drawing Sheets

Related U.S. Application Data continuation of application No. 16/399,658, filed on Apr. 30, 2019, now Pat. No. 10,639,389.

(60) Provisional application No. 62/664,744, filed on Apr. 30, 2018.

(51) Int. Cl.
  *A61L 2/10* (2006.01)
  *A61L 2/12* (2006.01)
  *A61N 5/00* (2006.01)
  *G01N 21/00* (2006.01)
  *G01N 23/00* (2006.01)

(52) U.S. Cl.
  CPC ..... *A61L 2202/122* (2013.01); *A61L 2202/14* (2013.01); *A61L 2202/24* (2013.01)

(58) Field of Classification Search
  USPC .......... 422/22, 24, 300; 250/453.11, 454.11, 250/455.11, 492.1
  See application file for complete search history.

(56) References Cited

U.S. PATENT DOCUMENTS

| | | |
|---|---|---|
| 5,260,020 A | 11/1993 | Wilk et al. |
| 5,275,668 A | 1/1994 | Dell et al. |
| 5,310,524 A | 5/1994 | Campbell et al. |
| 5,494,637 A | 2/1996 | Barlow |
| 5,711,921 A | 1/1998 | Langford |
| 5,785,678 A | 7/1998 | Griep et al. |
| 6,461,569 B1 | 10/2002 | Boudreaux |
| 7,537,589 B2 | 5/2009 | Tsukada et al. |
| 7,717,902 B2 | 5/2010 | Sauer |
| 7,905,831 B2 | 3/2011 | Noguchi et al. |
| 8,114,063 B2 | 2/2012 | Sacco et al. |
| 8,496,610 B2 | 7/2013 | Levenson et al. |
| 8,556,884 B2 | 10/2013 | Hong et al. |
| 8,933,416 B2 | 1/2015 | Arcand et al. |
| 8,946,653 B2 | 2/2015 | Victor et al. |
| 8,974,438 B2 | 3/2015 | Hong et al. |
| 9,168,354 B2 | 10/2015 | Hannon et al. |
| 9,421,290 B2 | 8/2016 | Victor et al. |
| 9,492,574 B2 | 11/2016 | Rasooly et al. |
| 9,550,005 B2 | 1/2017 | Lin et al. |
| 9,808,647 B2 | 11/2017 | Rhodes et al. |
| 9,865,018 B2 | 1/2018 | Bowne et al. |
| 9,877,176 B2 | 1/2018 | Gabel |
| 10,639,389 B2 | 5/2020 | Paul et al. |
| 10,850,062 B2 | 12/2020 | Vazales et al. |
| 11,027,112 B2 | 6/2021 | Kheir et al. |
| 2003/0017073 A1 | 1/2003 | Eckhardt et al. |
| 2005/0135965 A1 | 6/2005 | Williams et al. |
| 2005/0205206 A1 | 9/2005 | Lembersky |
| 2008/0159908 A1 | 7/2008 | Redmond |
| 2010/0286479 A1 | 11/2010 | Ashida et al. |
| 2011/0044848 A1 | 2/2011 | Wright |
| 2011/0224649 A1 | 9/2011 | Duane et al. |
| 2012/0230868 A1 | 9/2012 | Reddy et al. |
| 2013/0256560 A1 | 10/2013 | Yerby |
| 2014/0264074 A1* | 9/2014 | Victor ..................... A61L 2/10 250/455.11 |
| 2015/0231287 A1 | 8/2015 | Lin et al. |
| 2015/0362828 A1 | 12/2015 | Patel et al. |
| 2015/0366462 A1 | 12/2015 | Ramos |
| 2015/0374868 A1 | 12/2015 | Bruce et al. |
| 2016/0001037 A1 | 1/2016 | Hong et al. |
| 2016/0193375 A1 | 7/2016 | Aflamme et al. |
| 2017/0119915 A1 | 5/2017 | Lin et al. |
| 2017/0136209 A1 | 5/2017 | Burnett et al. |
| 2017/0165386 A1 | 6/2017 | Huang |
| 2017/0224952 A1 | 8/2017 | Barneck et al. |
| 2017/0252472 A1 | 9/2017 | Dang et al. |
| 2017/0252473 A1 | 9/2017 | Thompson et al. |
| 2018/0036510 A1 | 2/2018 | Tanghoej et al. |
| 2018/0071482 A1 | 3/2018 | Fitzpatrick et al. |
| 2019/0290791 A1 | 9/2019 | Baker et al. |
| 2019/0328915 A1 | 10/2019 | Paul et al. |
| 2020/0188543 A1 | 6/2020 | Etter et al. |
| 2020/0324006 A1 | 10/2020 | Paul et al. |
| 2021/0023348 A1 | 1/2021 | Matsushita et al. |
| 2021/0100982 A1 | 4/2021 | Laby et al. |
| 2021/0113725 A1 | 4/2021 | Etter et al. |

FOREIGN PATENT DOCUMENTS

| | | |
|---|---|---|
| CN | 213031135 U | 4/2021 |
| DE | 202011107059 U1 | 1/2013 |
| EP | 3308823 A1 | 4/2018 |
| EP | 2471569 B1 | 10/2018 |
| JP | 6535126 B2 | 6/2019 |
| KR | 20140139477 A | 12/2014 |
| KR | 101657873 B1 | 9/2016 |
| WO | 2020252045 A1 | 12/2020 |
| WO | 2021061661 A1 | 4/2021 |

OTHER PUBLICATIONS

Souvik Paul, CleanCath Catheter Sterilizer, https://designawards.core77.com/Strategy-Research/64780/CleanCath-Catheter-Sterilizer, visited Sep. 2, 2021.

besttechnologyinc.com, Automated Ultrasonic Medical Device Catheter Cleaning System, https://www.besttechnologyinc.com/case-studies/medical-device-catheter-cleaning-system/, visited Sep. 2, 2021.

Bardcare.com, Urological Products Product Catalog, visited Sep. 2, 2021.

180medical.com, The Full Guide to No-Touch Catheters, https://www.180medical.com/blog/the-full-guide-to-no-touch-catheters/, visited Sep. 2, 2021.

cincinnatichildrens.org, Sterilization of Urinary Catheters, https://www.cincinnatichildrens.org/health/s/steril-catheters, visited Sep. 2, 2021.

* cited by examiner

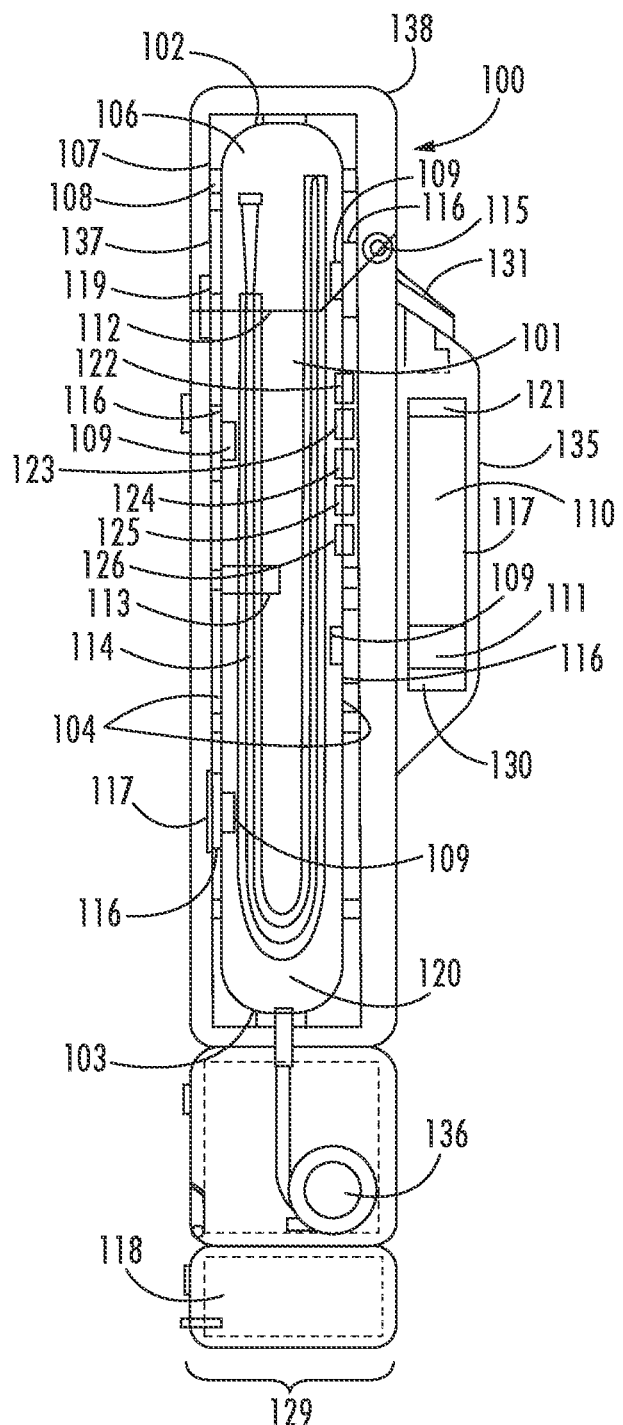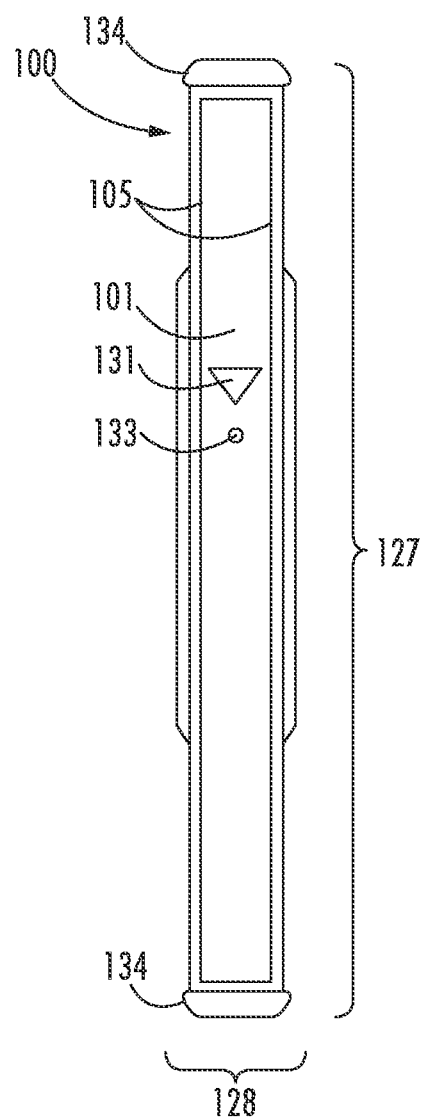
FIG. 1A
FIG. 1B

METHODS AND DEVICES FOR PORTABLE STERILIZATION AND CONTAINMENT OF REUSABLE URINARY CATHETERS

CROSS-REFERENCE TO RELATED APPLICATIONS

This application is a continuation of U.S. patent application Ser. No. 16/847,830, filed Apr. 14, 2020, which is a continuation of U.S. patent application Ser. No. 16/399,658, filed Apr. 30, 2019 and issued as U.S. Pat. No. 10,639,389 on May 5, 2020, which claims priority to U.S. Provisional Patent Application No. 62/664,744, filed Apr. 30, 2018, entitled Methods and Devices for Portable Sterilization and Containment of Medical Devices, which is incorporated herein by reference in its entirety and made a part hereof.

TECHNICAL FIELD

The present invention generally relates to sterilization radiation systems, and, more particularly, to methods and systems for urinary catheterization, urinary catheter sterilization, and combined data acquisition and deposition.

BACKGROUND OF THE INVENTION

Intermittent urinary catheters and catheter systems are well known in the art. While intermittent urinary catheters and catheter systems according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY

The present invention generally provides methods and devices for urinary catheterization, urinary catheter sterilization, and combined data acquisition and deposition.

According to one embodiment, a sterilizer for sterilizing one or more medical devices may include a housing including one or more walls defining a sterilization chamber for containing electromagnetic radiation and for the enclosing of the one or more medical devices, at least one electromagnetic radiation source comprising a plurality of electromagnetic radiation emitters arranged in an at least one array, and an internal control circuit for controlling a sterilization cycle. The housing may have one or more openings for receiving the one or more medical devices and a door that hinges open to allow individual access to the one or more medical devices. The door may provide a seal between the sterilization chamber and an external environment when closed. The emitters may be positioned to emit electromagnetic radiation within the sterilization chamber. The internal control circuit may include an RFID scanner for use with the one or more medical devices. The internal control circuit may also include a plurality of sensors that validate the sterilizer is completely closed during the sterilization cycle, prevent sterilization of non-system components, and prevent radiation emission into the external environment. The plurality of sensors may include a radiation sensor located in a hardest to sterilize location within the housing, wherein the sterilization cycle continues until the radiation sensor has received a radiation dose greater than a minimum radiation dose set within the internal control circuit. The sterilization chamber may including a liner with sterilizing radiation reflecting material adapted to reflect and distribute the radiation.

According to another embodiment, a sterilizer for sterilizing one or more medical devices may include a housing including one or more walls defining a sterilization chamber for containing electromagnetic radiation and for enclosing the one or more medical devices, one or more individualized trays that correspond to the one or more medical devices, at least one electromagnetic UV-C radiation source comprising a plurality of mercury-based UV-C emitting bulbs arranged in an at least one array and embedded within the one or more walls of the sterilization chamber, and an internal control circuit for controlling a sterilization cycle with sterilizer software. The housing may have one or more openings for receiving the one or more medical devices and a door that hinges open to allow individual access to the one or more medical devices. The door may provide a seal between the sterilization chamber and an external environment when closed. Each individualized tray may independently pivot out of the sterilizer for ease of loading by a user. The bulbs may be positioned to emit electromagnetic UV-C radiation within the sterilization chamber. The internal control circuit may include an RFID scanner that validates an authenticity of the one or more medical devices placed within the sterilizer and writes data to an RFID chip embedded in each of the one or more medical devices. The internal control circuit may further include a plurality of sensors that validate the sterilizer is completely closed during the sterilization cycle, prevent sterilization of non-system components, and prevent radiation emission into the external environment. The plurality of sensors may include a UV-C sensor located in a hardest to sterilize location within the housing, wherein the sterilization cycle continues until the UV-C sensor has received a UV-C radiation dose greater than a minimum UV-C radiation dose set within the internal control circuit. The sterilization chamber may include a liner with sterilizing radiation reflecting material adapted to reflect and distribute the UV-C radiation.

According to another embodiment, a method for sterilizing one or more medical devices using electromagnetic radiation may include: enclosing one or more medical devices in a sterilizer; scanning, by an RFID scanner within the sterilizer, the one or more medical devices placed within the sterilizer to validate the authenticity of the one or more medical devices; write, by the RFID scanner, data to an RFID chip embedded in each of the one or more medical devices; sealing the sterilization chamber with a door that hinges open to allow individual access to the one or more medical devices; starting a sterilization cycle with an internal control circuit for controlling the sterilization cycle with sterilizer software; and irradiating surfaces of the one or more medical devices with electromagnetic radiation from at least one electromagnetic UV-C radiation source. The sterilizer may include a housing with one or more walls defining a sterilization chamber for containing electromagnetic radiation. The sterilization chamber may include a liner with sterilizing radiation reflecting material adapted to reflect and distribute the radiation. The door may provide a seal between the sterilization chamber and an external environment when closed. The internal control circuit may include a plurality of sensors that validate the sterilizer is completely closed during the sterilization cycle, prevent sterilization of non-system components, and prevent radiation emission into the external environment. The plurality of sensors may include a UV-C sensor located in a hardest to sterilize location within the housing, wherein the sterilization cycle continues until the UV-C sensor has received a UV-C radiation dose greater than a minimum UV-C radiation dose set within the internal control circuit. The electromagnetic UV-C radiation source may comprise a plurality of mercury-based UV-C emitting bulbs arranged in an at least one array and embedded within the one or more walls of the sterilization chamber. The bulbs may be positioned to emit electromagnetic UV-C radiation within the sterilization chamber thereby destroying biological contaminants on the surfaces of the one or more medical devices.

According to yet another embodiment, a sterilization system may include one or more urinary intermittent catheters, one or more catheter insertion aids that mate with the one or more catheters and provide support and lubrication to the one or more catheters, and a sterilizer for sterilizing the one or more catheters and the one or more catheter insertion aids. The one or more urinary intermittent catheters may be made from UVC-transparent and flexible material. The one or more catheters may include a curved funnel and an RFID chip that contains authentication information and usage information. The one or more insertion aids may include a flexible insertion tip that matches a French size of the catheter. The one or more insertion aids may further include an RFID chip that contains authentication information and usage information. The sterilizer may include a housing including one or more walls defining a sterilization chamber for containing electromagnetic radiation and for enclosing the one or more catheters and the one or more insertion aids, one or more individualized trays that correspond to the one or more catheters and the one or more insertion aids, at least one electromagnetic UV-C radiation source comprising a plurality of mercury-based UV-C radiation emitting bulbs arranged in an at least one array and embedded within the one or more walls of the sterilization chamber, and an internal control circuit for controlling a sterilization cycle with sterilizer software. The housing may have one or more openings for receiving the one or more catheters and the one or more insertion aids and a door that hinges open to allow individual access to the one or more catheters and the one or more insertion aids. The door may provide a seal between the sterilization chamber and an external environment when closed. Each individualized tray may independently pivot out of the sterilizer for ease of loading by a user. The bulbs may be positioned to emit electromagnetic UV-C radiation within the sterilization chamber. The internal control circuit may include an RFID scanner that validates an authenticity of the one or more catheters and the one or more insertion aids placed within the sterilizer and writes data to the RFID chips in each of the one or more catheters and the one or more insertion aids. The internal control circuit may further include a plurality of sensors that validate the sterilizer is completely closed during the sterilization cycle, prevent sterilization of non-system components, and prevent radiation emission into the external environment. The plurality of sensors may include a UV-C sensor located in a hardest to sterilize location within the housing, wherein the sterilization cycle continues until the UV-C sensor has received a UV-C radiation dose greater than a minimum UV-C radiation dose set within the internal control circuit. The sterilization chamber may further include a liner with sterilizing radiation reflecting material adapted to reflect and distribute the UV-C radiation.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1A is a perspective cross-sectional side view of an illustrative embodiment of an apparatus according to one embodiment of the invention.

FIG. 1B is a front side view of the apparatus of FIG. 1A according to an embodiment of the invention.

Figure 2:
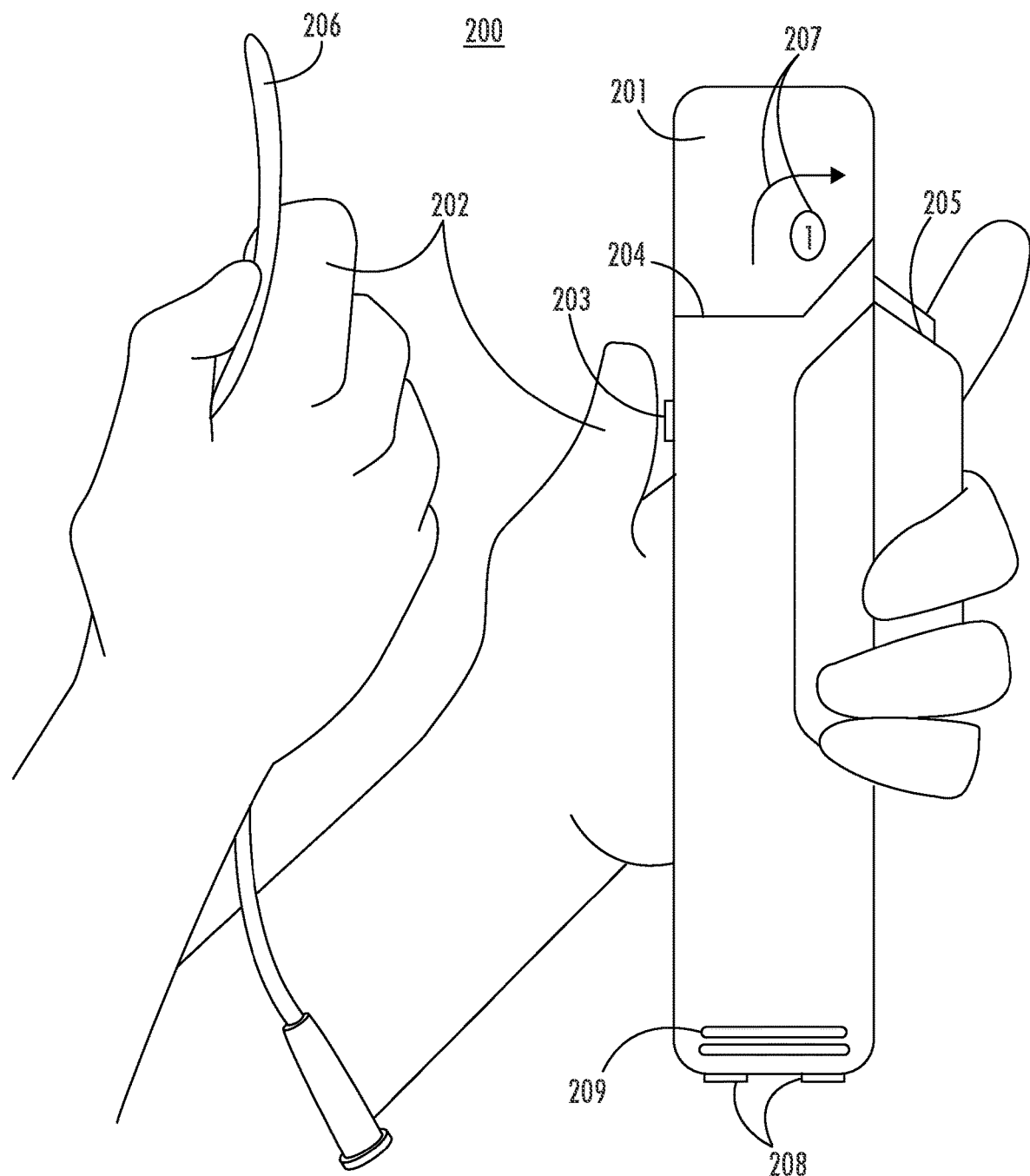
FIG. 2 is a perspective side view of an illustrative embodiment of an apparatus according to another embodiment held by a left hand of an individual and a medical catheter held in a right hand.

The above-mentioned and other features of the inventions disclosed herein are described below with reference to the drawings of the preferred embodiments. The illustrated embodiments are intended to illustrate, but not to limit the inventions.

DETAILED DESCRIPTION

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

In the following detailed description for purposes of explanation and not limitation, exemplary embodiments disclosing specific details are set forth in order to provide a thorough understanding of the present invention. It will be apparent, however, to one having ordinary skill in the art that the present invention may be practiced in other embodiments that depart from the specific details disclosed herein. In other instances, detailed description of well-known devices and methods may be omitted so as not to obscure the description of the present invention.

In medicine and therapeutic treatments, a catheter is a tube that can be inserted into a body cavity, duct, or vessel. Catheters thereby allow drainage, injection of fluids, diagnostic agents, and/or medicine, or access by surgical instruments. In most uses, a catheter is a thin, flexible tube (i.e. a "soft" catheter) and, in some uses, a larger, solid tube (i.e. a "hard" catheter). Various catheter tip designs are known including coudé tips, stepped tips, tapered tips, over-molded tips, split tips, and so forth. Catheters may include various accessories such as molded components, over-molded subassemblies, connecting fittings such as hubs, extension tubes, and so forth.

During and after use, catheters can be colonized by micro-organisms if the catheters come in contact with the user's unsterilized skin, specifically on the perineum and the tip of the urethra. The colonizing micro-organisms can multiply and form a biofilm layer within 24 hours of catheter use, during which they are metabolically active and viable. Catheters contaminated with said microorganisms are known to cause negative health outcomes such as UTIs when used without sterilization. It is known that while there are homemade means to sterilize catheters such as rinsing the used catheter followed by submerging in isopropyl alcohol for a five-minute duration, inconsistent rinsing and inappropriate post-sterilization storage causes re-contamination of catheters by exposing them to potential colonization by micro-organisms and leads to negative health outcomes for the user.

The invention relates to enabling medical device users (e.g., catheter users) concerned with sterilizing their products from bacteria and other microorganisms to use a portable germicidal device that utilizes radiation to sterilize the medical product(s), safely shields the user from radiation or other exposure during such sterilization, and provides sterile storage of the catheter or other medical product until needed. Moreover, the devices, systems, and methods according to the invention preferably provide increased standardization for sterilizing catheters or other products to reduce the risk of inadequate and/or inconsistent sterilization.

One aspect of the invention relates to systems and/or apparatuses capable of sterilizing medical products, preferably catheters, or other products using radiation. The apparatus of the present invention can be efficiently configured and designed to provide sterilization of the surfaces of a medical device by emitting radiation in a range sufficient and effective to destroy contaminants including pathogens and microorganisms. According to one preferred embodiment, radiation emitting diodes are placed in an array such that radiation is emitted into the interior of the apparatus enclosing the medical device for sterilization. The array may be configured linearly, circularly, or rectangularly to form a matrix of diodes and may be located on, within, or behind the interior wall of the sterilization chamber. Preferably, the systems and/or apparatuses can repeatedly sterilize medical products (e.g., catheters) without damaging them.

One preferred embodiment relates to a device comprising an interior chamber adapted to enclose a medical device and adapted to irradiate the medical device with radiation to sterilize the medical device.

Another embodiment relates to an apparatus for sterilizing a medical device, the apparatus comprising: (a) one or more walls defining an interior for containing radiation and for enclosing the medical device; (b) at least one radiation source comprising a plurality of radiation emitting diodes, wherein the diodes are positioned to emit radiation within the interior; (c) a power source capable of providing energy to the diodes; and (d) one or more openings adapted to provide a seal between the interior and external environment when closed.

Another aspect of the invention relates to methods of sterilizing one or more medical devices or other products using radiation. One embodiment of the invention relates to a method for sterilizing a medical device using ultraviolet (UV) radiation comprising: (a) enclosing the medical device in a chamber; (b) sealing the chamber; and (c) irradiating surfaces of the medical device with UV radiation thereby destroying biological contaminants on the surfaces of the medical device.

Another embodiment of the invention relates to a method for sterilizing a medical device using microwave radiation comprising: (a) enclosing the medical device in a chamber; (b) sealing the chamber; and (c) irradiating surfaces of the medical device with microwave radiation thereby destroying biological contaminants on the surfaces of the medical device.

Another embodiment of the invention relates to a method for sterilizing a medical 20 device using thermal radiation comprising: (a) enclosing the medical device in a chamber; (b) sealing the chamber; and (c) irradiating surfaces of the medical device with thermal radiation thereby destroying biological contaminants on the surfaces of the medical device.

Another aspect of the invention relates to a system comprising at least one apparatus or device as described herein and one or more additional components to facilitate the convenient sterilization of one or more medical products using radiation.

The foregoing has outlined some of the aspects of the present invention. These aspects should be construed strictly as illustrative of some of the more prominent features and applications of the invention, rather than as limitations on the invention.

Many other beneficial results can be obtained by modifying the embodiments within the scope of the invention. Accordingly, for other objects and a full understanding of the invention, refer to the summary of the invention, the detailed description describing the preferred embodiment in addition to the scope of the invention defined by the claims and the accompanying drawings. The unique features characteristic of this invention and operation will be understood more easily with the detailed description and drawings. It is to be understood that the drawings are for illustration and description only and do not define the limits of the invention.

It is known that in some settings and some circumstances, radiation of various wavelengths can inactivate microorganisms such as bacteria, virus, fungi, protozoa, algae, and so forth using electromagnetic waves of various wavelengths and bands, including ultraviolet light, thermal radiation, and microwave radiation. Ultraviolet light is typically characterized in the following wavelength bands: ultraviolet-C (UVC) having a wavelength of 100 to 280 nm, ultraviolet-B (UVB) having a wavelength 280 to 320 nm, and ultraviolet-A (UVA) having a wavelength of 320 to 400 nm. Microwaves are characterized with a wavelength between 1 mm to 1 m, where most conventional microwave ovens operate near a 12 cm wavelength (2450 MHz). Thermal radiation is a broadband type of emission that isn't typically characterized by its wavelength band and most often referred to as heat. In all cases, these types of radiation are often used to sterilize surfaces and/or objects in hospital settings.

It is noted all forms are radiation are dangerous for humans with substantial exposure with outcomes dependent on the wavelengths emitted. Dependent on the wavelength, UV can be absorbed by DNA extremely well causing DNA to mutate, which is the primary mechanism used to inactivate microorganisms through UV. However, this mechanism also applies to humans, where high human exposure to UV causes radiation sickness, resulting in symptoms such as eye irritation and reddening, skin irritation, nausea, fever, disorientation, hair loss, cancer, and, in extreme cases, death. Microwaves and thermal radiation can cause molecules such as water to vibrate and heat up creating hydrothermal pressure within a cell body, causing damage to the cell wall, breakage of genomic DNA, and thermal coagulation of cytoplasmic proteins resulting in cell death and/or inactivation. Again, this phenomenon applies to human cells as well and high exposure to microwave and/or thermal radiation can result in burn injuries and co-morbidities that can result in death. For these reasons, high doses of any radiation must be prevented from striking humans.

One or more of the inventions relate to improved apparatuses, systems, and methods for sterilizing medical or other products using radiation and similar energy.

One aspect of the invention relates to apparatuses having an interior or inner chamber adapted to sterilize a medical device, preferably a portable device adapted to be used by individuals, preferably at home or at their convenience.

Another embodiment relates to a device comprising an interior chamber adapted to enclose a medical device and adapted to irradiate the medical device with radiation to sterilize the medical device.

Another embodiment relates to an apparatus for sterilizing a medical device, the apparatus comprising: (a) one or more walls defining an interior for containing radiation and for enclosing the medical device; (b) at least one radiation source comprising a plurality of radiation emitting diodes, wherein the diodes are positioned to emit radiation into the interior; (c) a power source capable of providing energy to the diodes; and (d) one or more openings adapted to provide a seal between the interior and 25 external environment when closed.

Referring now to the Figures, there is shown a variety of embodiments of intermittent urinary catheters and catheter systems. Additionally, each of these variations may have a variety of optional equipment, components, and features associated therewith.

FIG. 1A shows a cross sectional view of one embodiment of an apparatus 100 according to the invention. As illustrated, the apparatus 100 includes a sterilization chamber 101 having interior 106 and the medical device 114 positioned within the interior 106.

The interior 106 preferably comprises a top wall 102, a bottom wall 103, opposing side walls 104 and opposing side walls 105 (FIG. 1B), which define the interior 106 of the chamber 101. Alternatively, interior 106 can be configured with curved inner wall (e.g., egg-shell shaped with curved sides and top and bottom). The sterilization chamber 101 is protected by housing 107. As depicted, a preferred embodiment of the invention is a rectangular block with rounded edges where one end has one or more openings and has one or more switches 131 on one of the exterior walls. Furthermore, there is a structural skeleton 108 that is used to insulate the interior chamber 101 from the housing 107, provide additional rigidity, and enhance heat dissipation.

Preferred embodiments are portable. The height/length 127, thickness 128, and width 129 are denoted in FIGS. 1A and 1B. Preferably, the overall dimensions of the apparatus housing are: height 127 of 5" to 18" (preferably 6" to 16"), length 128 of 1.5" to 6" (preferably 1.5" to 5"), width 129 of 1" to 6" (preferably 1.5" to 5"). Preferably, the dimensions for the interior are: Height of 4" to 14" (preferably 5" to 12"), length of 0.75" 15 to 4" (preferably 1" to 3"), width of 0.75" to 4" (preferably 1" to 3").

According to preferred embodiments of the present invention, one or more walls of the interior of the chamber are radiation reflective as to distribute radiation throughout the interior of the chamber. The spectral reflectance of this chamber should be no less than 80% reflective to the emitted radiation wavelengths. Preferably, the interior wall comprises aluminum.

The apparatus comprises multiple openings that can open and close: one to insert the medical device 114 into interior 106 and one can be opened to allow access to a cavity 118 in the housing used to store replaceable medical or cleaning supplies, preferably sterile gloves, isopropyl alcohol, or betadine. Preferably, the apparatus includes lid 138 that pivots about a hinge 115 allowing the lid to open or close. A sealing gasket 112 provides a releasable hermetic seal allowing sterile storage of the medical device 114 within interior 106. Once sealed, a magnetic lock 119 is used to lock the apparatus during operation and storage. A medical device 114 is shown positioned within the chamber with anchored support 113 on the side wall 104.

The closed interior 106 compartment can substantially eliminate stray energy from escaping the interior 106 while eliminating fluid exchange with environment. Any suitable UV reflective material may be incorporated in the composition of the interior 106 wall or surface during manufacture or assembly. Polished aluminum could be utilized as a surface material because of its high reflectivity. The sealing gasket 112 is made of UV stable material such as silicone.

Disposed within the apparatus 100 are individual ultraviolet light emitted diodes (UVLEDs) 109 placed in an array such that radiation is emitted into the interior. Preferably, the diodes have a peak emission wavelength range of 240 to 320 nm and more preferably 285 nm. Preferably, the diodes have a radiant flux range of 0.1 mW to 100 mW. The sterilization chamber 100 of the present invention can provide the necessary decontamination and sterilization measures to effectively ensure a 5-log reduction [99.999%] of any residual biological contaminants on the exposed or hard-to-reach crevices of a medical device. Preferably, multiple UVLEDs 109 are arranged on or along one or more of the walls and there is sufficient space to the opposing wall to allow reflection of the irradiation allowing irradiation of multiple surfaces of a target consistently. For example, preferably LEDs 109 are recessed into the walls of the interior 106 and configured to emit UV into the interior 106. A heat sink 116 is affixed to the UVLEDs to improve heat dissipation during operation. In the depicted embodiment, the heat sinks are applied to the outer surface of walls comprising interior 106 and in direct contact with the non-emitting surface of the UVLEDs 109. In another embodiment, one heat sink may be applied to an array of diodes. In another embodiment, one heat sink may be applied per wall of the sterilization chamber.

A power supply 110 provides energy to the UVLEDs 109 and preferably comprises an internal supply of energy such as a rechargeable battery. A microcontroller 111 is used to control operation of apparatus electronic components such as the UVLEDs 109. This microcontroller 111 receives information from a switch 131 which enables to the user to open and close the magnetic lock 119. The microcontroller also receives information from a UV sensor 122, humidity sensor 123, temperature sensor 124, light sensor 125, and pressure sensor 126. This information is used to determine whether the apparatus is in operation and whether the apparatus is functioning out of expectation. For instance, visible light should not be detected within the chamber once the chamber is sealed and locked. If the switch is activated and visible light is detected by the light sensor, the microcontroller will not allow the UVLEDs to operate. Other events include but are not limited to rapid temperature swings, rapidly decreasing humidity during operation, detected pressure lower than atmospheric pressure.

A serial code reader 137 is used wherein a user would scan a serial code related to the medical device prior to sterilization to track the number of times the medical device was irradiated in the apparatus. A memory card 121 is used to log this event data. A wireless transmitter 130 is used to transmit this data to an external source such as a cellphone or a laptop.

Current operation of the apparatus can be viewed through the indicator LED 133. For example, when the unit is not in operation and not sealed, the LED would be off. When the unit is sealed but not in operation, the LED would shine blue. When the unit is sealed and in operation, the LED would pulse purple. When the unit is sealed and finished with operation, the LED would shine green.

Potting material 117 is used to encapsulate electronic components in order to mitigate radiation exposure, improve heat dissipation, and resist shock and vibration. As depicted, the potting material 117 is applied as insulation in the volume or space between the housing 107 and sterilization chamber 106, for example where electronic components are housed. Additional insulating material may be used to fill the cavities between the exterior walls of the apparatus and the sterilization chamber to further insulate the apparatus interior from the exterior environment.

As depicted in FIGS. 1A and 1B, the apparatus 100 further comprises a textured grip 135 to provide an ergonomic handle, allowing safer handling of the apparatus. The apparatus further comprises an exterior bumper guard 134 around the housing at each end to protect the apparatus from falls and shocks.

As depicted in FIGS. 1A and 1B, a micro fluid pump 136 is used to pump fluid into and out of the chamber. In this embodiment, the fluid pump 136 is used to pump a mixture of water, hydrogen peroxide, and silver particles to enhance sterilization. It is known that hydrogen peroxide and silver particles enhance DNA inactivation when using in conjunction with UV radiation. After sterilization, the micro fluid pump 136 will remove remaining fluid within the chamber. Micro fluid pump 136 can either be included within a unit that is attached to the apparatus as in FIG. 1A or integrated within the apparatus (e.g., enclosed within housing 107, preferably adjacent interior 106) as in FIG. 1B. For example, the apparatus may have a port to connect to a fluid pump to provide fluid to the interior chamber.

According to one embodiment of the present invention, the exterior of the apparatus housing further comprises one or more external supports, legs, tabs or grips on the exterior surface of the housing to allow the unit to stand upright and in a stable manner.

Another preferred embodiment relates to an apparatus for sterilizing surfaces of medical devices from contamination by microorganisms, the apparatus comprising: one or more walls which define an interior chamber for containing UV radiation such that the interior chamber can be proportionally sized to enclose target medical device requiring sterilization; a housing for the interior chamber with sufficient space to accommodate electronic circuitry and components; a source of radiation comprising a plurality of LEDs such that the LEDs can be positioned in relation to the interior chamber and/or the one or more walls; a power supply providing energy to the LEDs such that the LEDs emit UV radiation into the interior chamber; and one or more seals such as a gasket or O-bearing positioned to provide a hermetic seal for the interior chamber, preventing fluid and microorganism exchange between the interior chamber of the apparatus and the exterior environment, so that the plurality of UV LEDs substantially irradiate all surface areas of the target medical device with UV radiation and the apparatus further provides sterile storage of medical device while being sterilized and thereafter.

FIG. 2 shows an external view of an apparatus with a medical device according to one embodiment and a user hand for scale. As illustrated, the system 200 includes the sterilization apparatus 201, medical device 206, and a user hand 202. The sterilization apparatus 201 is shown in a user hand 202 to demonstrate the scale of portability of this embodiment, though it is again noted that this is for the purposes of explanation and not a limitation. As illustrated, a medical device 206 may be removably positioned to and from the interior of the sterilization apparatus 201. External switches 203 control the opening and closing through electrical controls. A sealing gasket 204 is used to create a hermetic seal to maintain a sterile interior environment before, during, and after irradiation. A textured grip 205 is positioned to allow for optimal grip for users with low hand dexterity and grip strength. Slippage grips 208 are used to reduce slippage when the apparatus is placed on a smooth surface. Preferably, both the textured grip and slippage grips are to be made of a durable and malleable material such as a silicone. Instructions 207 are placed on the exterior to guide the user to the correct procedure. In this preferred embodiment, the instructions are printed though alternatively, the instructions may also be preferably embossed. Personal identification 209 is printed on the outside to allow users to identify their apparatus. Alternatively, the personal identification may also be preferably embossed.

Figure 3:
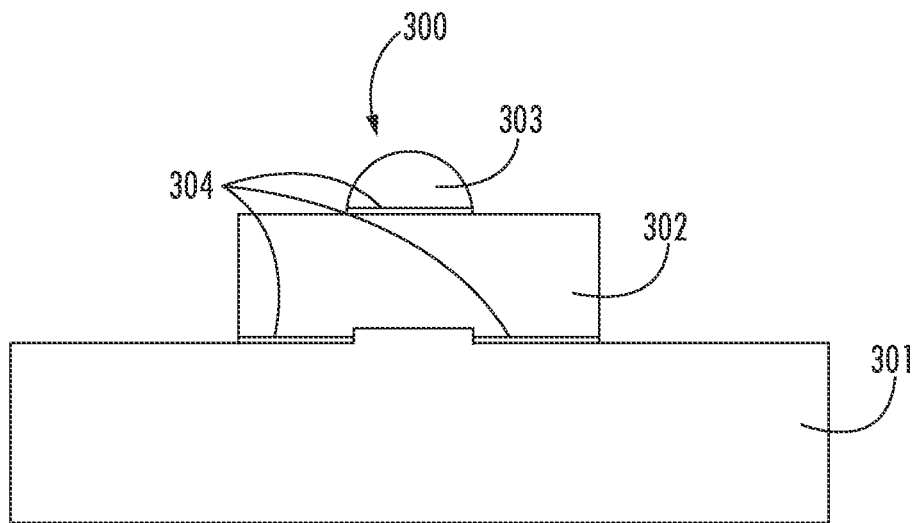
FIG. 3 is a perspective side schematic view of an embodiment of a light source sub-assembly according to another embodiment of the invention.

In preferred embodiments of the present invention, a holster or clip (not shown) may be included to allow user to carry or mount or clip the apparatus 100 on their person or an object such as a wheelchair, as shown in FIG. 3 (discussed below).

According to the invention, the apparatus can be designed to be portable (both small and light) and easy to use. Preferably, the medical device is adapted for use by an individual (e.g., in the individual's home) and/or for common everyday use environments such as outdoors, while at work, or traveling. Preferably, the medical device is adapted for insertion into a patient (e.g., a catheter). Preferably, the medical device is adapted to be used by the patient. Preferably, the medical device is CLIA waived. Preferably, the medical device is adapted for home use. Preferably, the device does not require calibration or more than five steps to complete (e.g., open, insert medical product, close, sterilize and remove sterilized product).

According to preferred embodiments, the medical device is made from a material (e.g., plastic or glass) that is translucent to the radiation used for sterilization. Preferably, the medical device comprises plastic or glass. More preferably, the medical device consists essentially of plastic or glass. Preferably, the medical device comprises a tube, more preferably a plastic tube. Preferably, the medical device is a tube having a length ranging between 4-18", preferably a length ranging between 6" to 16". Preferably, the medical device is flexible (e.g., capable of being bent for insertion into interior as shown in FIGS. 1A and 1B). Preferably, the radiation comprises induced high energy UV-B exposure. Preferably, the radiation comprises induced high energy UV-C exposure. Preferably, the radiation comprises UV radiation in the range between 100 nm to 390 nm. Preferably, the radiation comprises induced high energy thermal exposure. Preferably, the radiation comprises induced thermal radiation in the range between 150 and 450 degrees Fahrenheit. Preferably, the radiation comprises induced high energy microwave exposure. Preferably, the radiation comprises induced microwave radiation in the range between 1 millimeter and 1 meter.

According to preferred embodiments, the type of radiation and intensity is optimized for the type of medical or other product being sterilized and the microorganisms targeted. According to one example, the use of UV radiation at 0.01-10 J/cm2 for a 5-log reduction of *Salmonella typhimurium*. Another example would be use of –12 minutes of 1200 watt microwave, preferably 0.4 MJ. It is noted that delivered dose is dependent on view factor and heat transfer coefficient.

According to preferred embodiment, the apparatus is adapted for and/or the method of sterilizations uses interior chamber temperatures ranging from 150 to 450 (preferably 250 to 350) for a period of time ranging from 0.5 to 15 mins (preferably 1.5 to 10 minutes) to achieve sterilization. Preferably, the radiation, duration, and temperature ranges selected are optimized for inactivating pathogens such as, but not limited to, *Escherichia Coli*, Enterococci, *Enterobacter, Klebsiella pneumoniae, Pseudomonas aeuruginosa, Proteus mirabilis, Staphylococcus aureus*, and *Candida Albicans*. Preferably, the radiation from the radiation source inactivates microorganismal contaminants on the surfaces of the medical device, more preferably inactivates 95% of the microorganismal contaminants on the surfaces of the medical device, even more preferably at least 99%, even more preferably 99.99%, and most preferred 100% deactivated (e.g., no detectible active microorganismal contaminants).

The apparatuses according to the invention include a mechanism for generating and/or transmitting radiation or other energy into the interior of the apparatus to sterilize the medical device enclosed therein.

According to one embodiment, the apparatus comprises diodes configured to generate and/or emit radiation into the interior or sterilization chamber of the apparatus. According to one preferred embodiment, the diodes generate and/or emit thermal radiation. According to another preferred embodiment, the diodes generate and/or emit UV radiation. According to another preferred embodiment, the diodes generate and/or emit thermal radiation. According to another preferred embodiment, the diodes generate and/or emit microwave radiation. Preferably, the plurality of diodes is arranged in at least one array. Preferably, the plurality of diodes is embedded within the one or more walls of the interior. Preferably, the plurality of diodes is distributed throughout the inner surface of the interior.

According to preferred embodiments, the radiation source comprises a ball or hemispherical lens system for optimal launch of radiation into the interior and/or to protect the diodes from any fluids in the interior. Preferably, the radiation source comprises a UV transparent optical window for separating the fluid in the interior containing the medical device from the diode.

A cross-sectional side view of the light source sub-assembly according to one preferred embodiment is illustrated in FIG. 3. As illustrated, the light source sub-assembly 300 includes a UVLED 301, UV transparent window 302, and hemispherical lens 303.

The light source assembly 300 is positioned through apertures within the interior chamber 106 walls (e.g., recessed into the interior walls). The UV transparent window 302 separates the interior chamber 106 from the UVLED 301 to optimize light source operational lifetime by reducing exposure to potential user error and/or mechanical shock. The hemispherical lens 303 allows for a wider viewing angle resulting in optimal launch of the UVLED 301 irradiation into the interior 106. In this preferred embodiment, an adhesive 304 is used to attach the UVLED 301 to the UV transparent window 302 and the UV transparent window 302 to the hemispherical lens 303. The adhesive is made of a UV transparent material to allow the UV radiation to travel through the adhesive with minimal loss.

Modifications of the present invention may also include incorporating any type of LED, particularly those being developed to accommodate other ranges of wavelengths for sterilization. As a cost-effective choice, LEDs continue to be developed to improve their energy efficiency. Developments of organic light emitting diodes (OLEDs) could also be a possibility for being included in the present invention. The luminous efficiency which has led to development of organic light emitting diodes could also influence super-bright UV OLEDs to be developed for the present application. However, other UV light sources can also be used. According to preferred embodiments, the diodes are removable and may be replaced by an end user or a qualified technician.

According to preferred embodiments, the apparatus is comprised of components (e.g., interior chamber, housing, circuitry, pump, etc.) and preferably, the components are modular and may be replaced by an end user or a qualified technician. According to additional embodiments, the interior or inner chamber of the apparatus is further adapted to improve the radiation sterilization.

According to preferred embodiments, the one or more walls of the interior comprises a reflective coating or material adapted to reflect and distribute the radiation. Preferably, the reflective coating or material comprises optically diffuse materials for spectral reflectance. Preferably, a coating or material providing interior reflectance. Alternatively, the walls or entire interior can be made using material proving reflectance (e.g., the interior chamber is made of aluminum).

The apparatus preferably includes at least one opening or aperture for inserting and removing the medical device(s). Preferably, the apparatus further comprises a joint adapted to close and open the one or more openings allowing a user to insert and remove the medical devices from the interior. Preferably a kinematic joint, such as a hinge is used. FIGS. 1A and 1B shows hinge 115 which allows lid 138 to open. FIG. 2 depicts the rotation of the lid to open the apparatus. Alternatively, the interior is comprised of two or more mated components containing one or more sealing components to prevent fluid and microorganism exchange from the exterior environment and the interior. Preferably, the apparatus further comprises a containment system for holding the medical device after sterilization and/or for holding a new replacement medical product.

According to one preferred embodiment, the apparatus comprises a container for holding the medical device to protect the medical device from contact contamination after removal from the interior within the apparatus, wherein the container is proportionally sized to enclose the medical device and inside the interior. Preferably, the container is a tube. Alternatively, the container is a bag or a box. Preferably, the container is made of polyurethane, silicone, fluoropolymer or composite (preferably PTFE, FEP, PVDF). Preferably, the container has an opening for the medical device, even more preferably an opening that can open and close.

According to preferred embodiments, the container is within the apparatus housing or otherwise integrated within the apparatus. Alternatively, the container is attachable to the apparatus (e.g., via clips) or is a separate component to be used with the apparatus.

Figure 4:
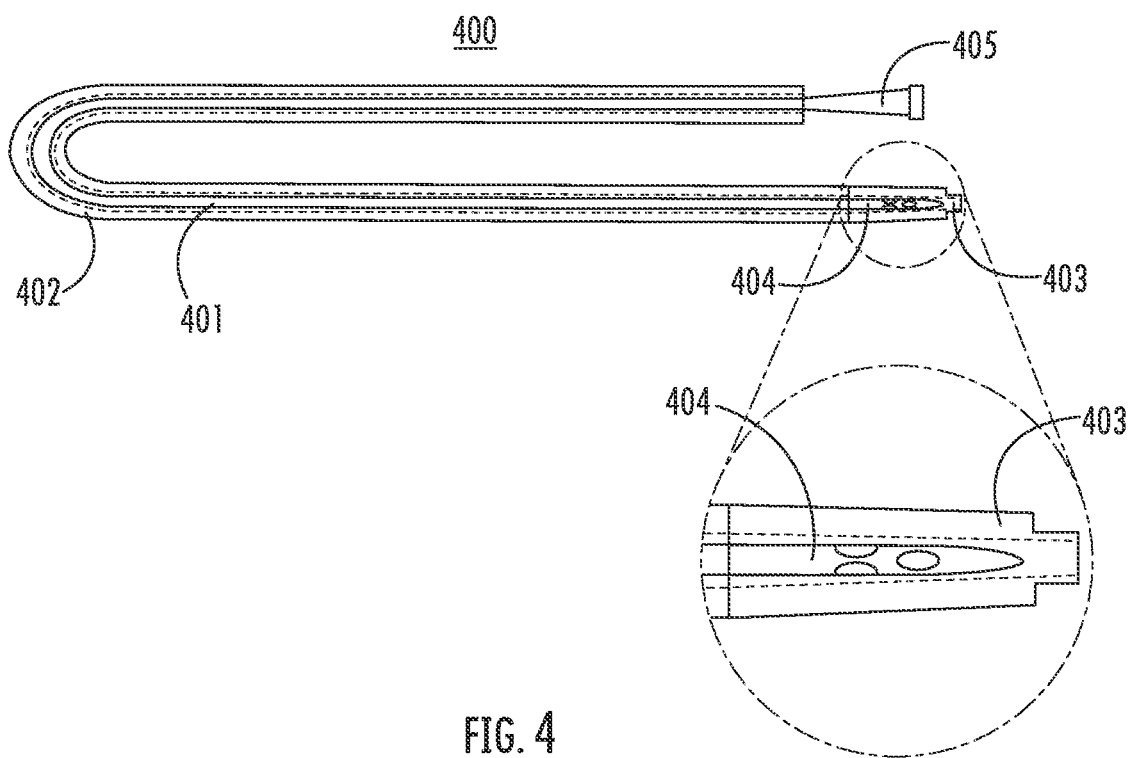
FIG. 4 is a cross sectional side view of an illustrative embodiment of a medical device, a contamination container enclosing the medical device, and an introducer tip.

According to preferred embodiments, the apparatus includes a container adapted to hold the medical device and is also adapted to be enclosed within the interior sterilization chamber. FIG. 4 shows container sub-assembly 400 comprising a medical device (which in this embodiment is a catheter) 401, a contamination container 402, and an introducer tip 403. The catheter 401 is fed through the contamination container 402 to minimize contact contamination post-irradiation. An introducer tip 403 is placed at the end of the in vivo portion 404 to allow guided handling during insertion of medical device. The ex vivo portion 405 is at the other opening of the container. This sub-assembly 400 is entirely placed into the interior of the apparatus to be irradiated and thus sterilized and the sub-assembly 400 can then be handled with reduced risk of contact contamination during insertion. An alternative embodiment of contamination container 402 allows the medical device to be inserted into the container such that only the in vivo portion of the device is inserted into the sterilization chamber for irradiation. The container 402 also allows the sterilized medical device to be removed from the apparatus and protected against contamination.

According to preferred embodiments, the apparatus further comprises a structural material or composite backing the interior to enhance structural rigidity. According to preferred embodiments, the apparatus further comprises a structural material or composite backing the interior to enhance thermal dissipation. According to preferred embodiments, the apparatus further comprises a structural material or composite backing the interior to enhance exclusion from and of exterior environment. For example, the structural material can be in the form of a housing for the interior and inner components of apparatus (e.g., diodes and circuits). Alternatively, the structural component can be in the form of a "spine" along the length of the apparatus.

According to preferred embodiments, the apparatus further comprises a housing fitted around the interior walls. Preferably, the housing is made of chemically or microbially resistant material. Preferably, the housing is made of one or more materials selected from the group consisting of aluminum, polyurethane, and rubber. Preferably, the housing has one or more openings, preferably aligned with an opening of the interior chamber. Preferably, the housing has one or more cavities for holding sterilization reagents or fluids, medical devices, etc. Even more preferably, the cavities have one or more openings that can be opened and closed. Preferably, the one or more cavities are located between the housing and the interior and the one or more cavities is filled with material to insulate the interior from the exterior environment.

According to preferred embodiments, the interior comprises a support structure to fasten or secure the medical device to allow consistent placement of the medical device within the interior. Preferably the support structure is made of radiation reflective and/or radiation stable materials, such as aluminum. Preferably, the interior or inner chamber is proportionally sized to enclose the medical device.

Figure 8:
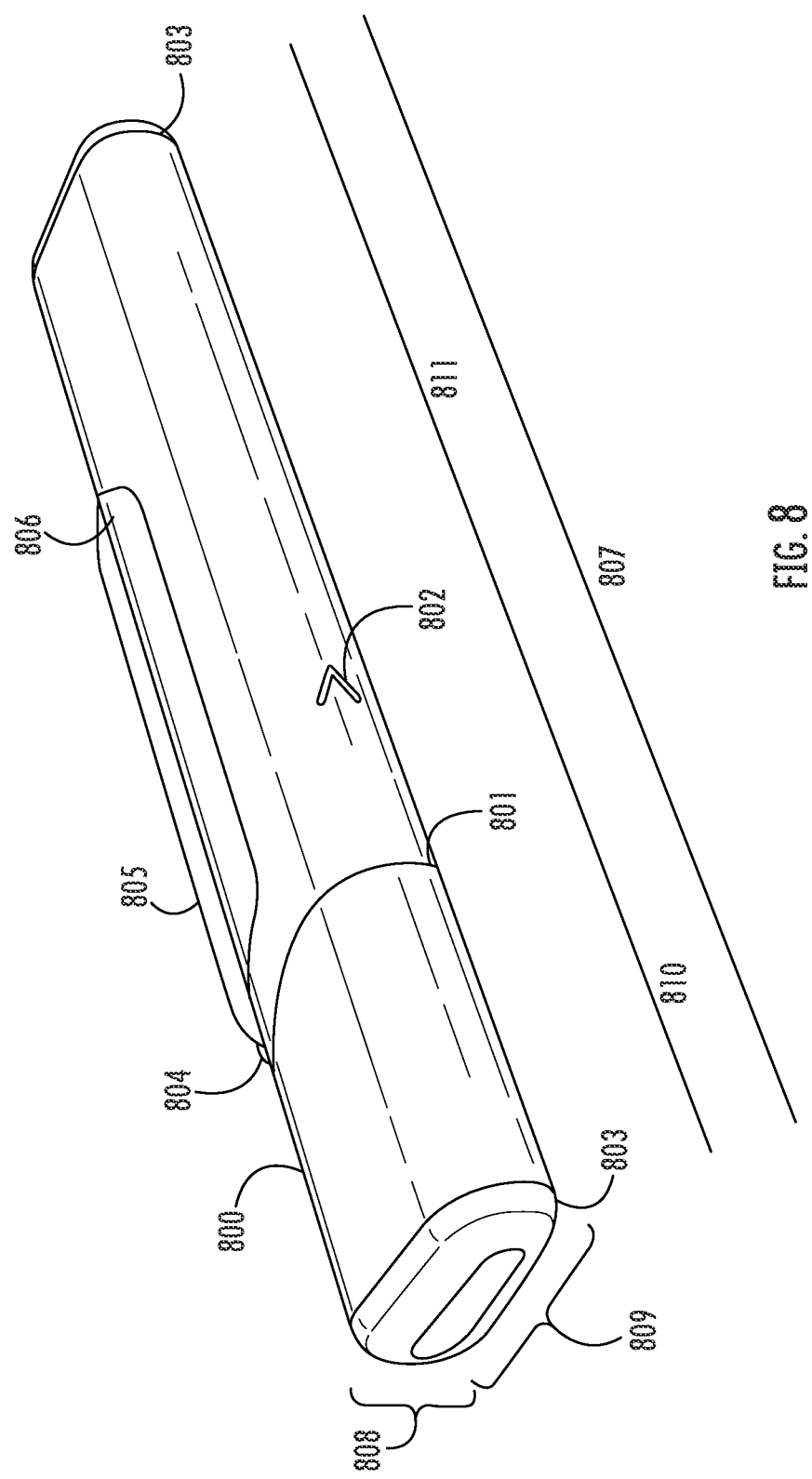
FIG. 8 is a perspective side view of an apparatus according to one preferred embodiment of the invention.
Figure 9:
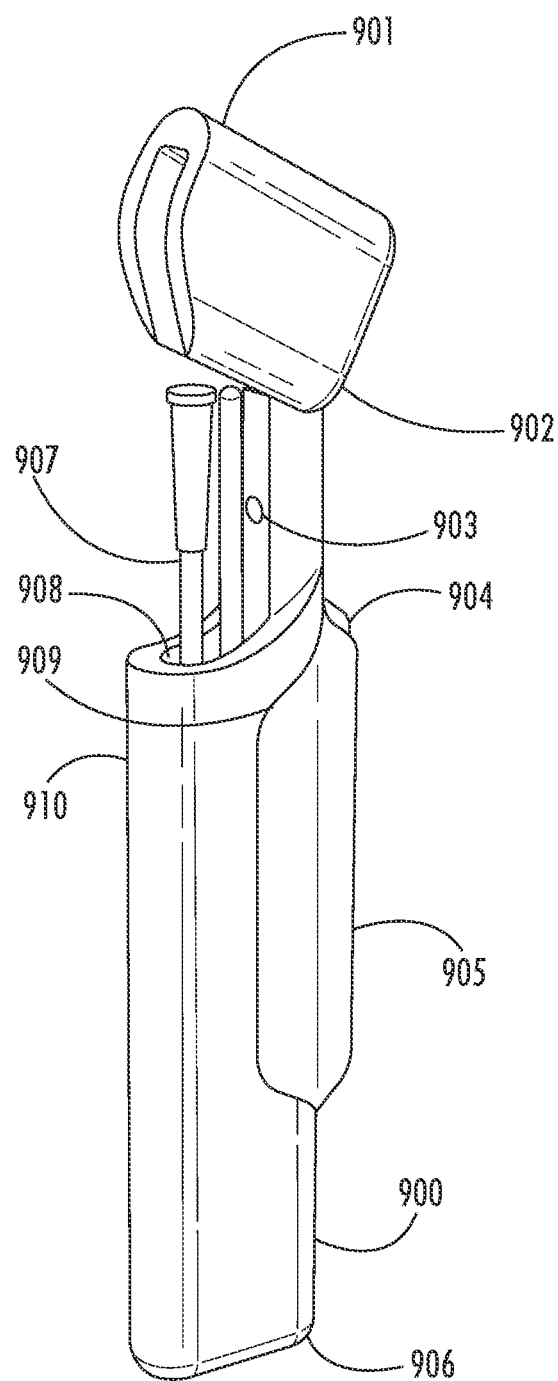
FIG. 9 is a perspective front view of an illustrative embodiment of the apparatus with the lid open.

According to preferred embodiments, the opening or lid used to insert the medical device comprises one quarter to one third of the overall height of the apparatus as depicted in FIG. 9 (and also depicted in FIG. 1 and FIG. 8) such that the user has greater accessibility to the medical device when the apparatus is open and will be able to remove the medical device more easily than a lid comprising only the top wall of the housing.

FIG. 9 shows the apparatus 900 further comprises a lid 901 that rotates around a kinematic hinge 902 to provide access to the medical device 907 when the apparatus 900 is open. In this embodiment, the apparatus 900 further comprises UVLEDs 903, external switch 904, exterior grip 905, external bumper guard 906, interior 908, slippage guards 909, and indicator LED 910.

According to preferred embodiments, the apparatus is modified such that when the apparatus is opened, the bottom wall of the interior is pushed towards the opening therefore pushing any medical devices housed within the interior towards the opening. The control mechanism in this case is a motor controlled linear actuator and alternate forms include but not limited to spring loading, pneumatic controls, and magnetic rail (e.g., the interior chamber lifts up so the catheter comes out; potentially spring loaded or motor controlled or pneumatic).

According to preferred embodiments, one or more button switches are two-state depressible such that the button is seated in a neutral position when untoggled and seats in a depressed position when toggled until the intended operation is completed or interrupted. (e.g., pressable buttons with locking states; depressed in one state; upright in the other).

According to preferred embodiments, one or more openings to the apparatus will be modified such that the medical device can be simultaneously removed from the interior and a lubricant is applied to the exterior surface of the medical device during removal. This is intended to allow users to lubricate the medical device without the need of additional handling (e.g., self-lubricating pull out method). The lubricant may further comprise of or be mixed with a pharmaceutical agent intended for reducing active pathogens post-sterilization (e.g., the device includes the ability to disperse pharmaceuticals on catheter as it lubricates). Alternatively, the pharmaceutical agent may be intended to counteract inflammation.

According to preferred embodiments, one or more openings has a self-closing door such that the opening will remain closed unless an object pushes with sufficient force to open the door and the door will close the opening when there is no force applied to the door. Furthermore, the apparatus has a motor-controlled mechanism to feed the medical device through the opening with a self-closing door (e.g., self-loading system).

According to preferred embodiments, the apparatus further comprises a pump (preferably a fluid pump) to pressurize or depressurize the interior.

Figure 6:
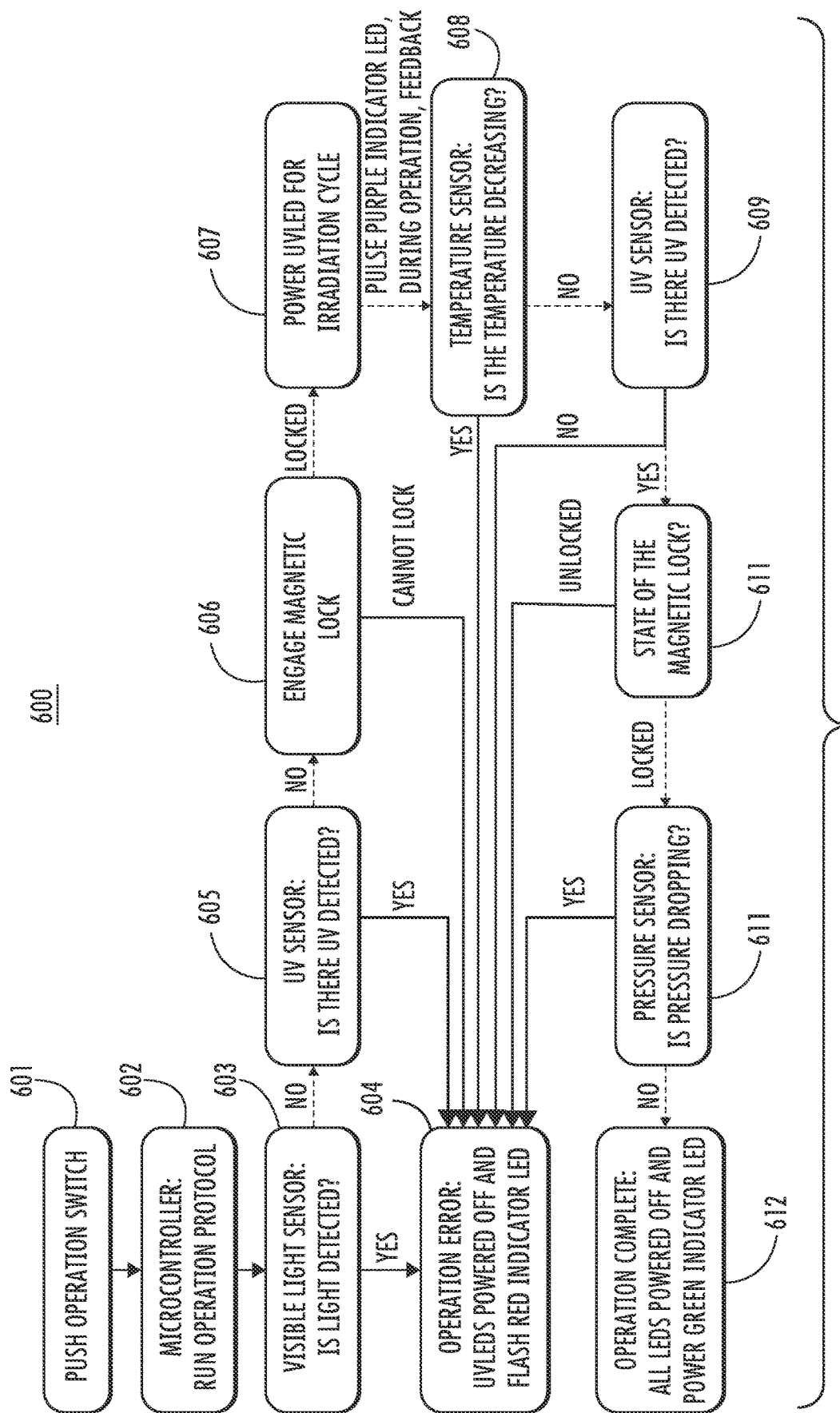
FIG. 6 is a logic block diagram describing the mechanics of the electronic controls of an apparatus according to one embodiment of the invention.

According to preferred embodiments, the apparatus comprises an internal control circuitry to operate and/or control and/or measure the operation of the device and/or open/close the opening. For example, a logic block diagram for the electronic controls according to one embodiment is illustrated in FIG. 6. The logic sequence 600 is initiated by pushing the operation switch 601. This communicates with the microcontroller 602 which runs the operation protocol. Expected operational status is denoted by dashed arrows while error pathways are denoted by solid arrows. The microcontroller detects whether light or UV is detected within the chamber via visible light sensor 603 and UV sensor 605. If either is detected above a set threshold, an operation error 604 occurs where the UVLEDs are powered off and a red indicator LED is flashed as a visual cue for the user. If neither is detected above a set threshold, the magnetic lock engages 606 followed by the UVLED irradiation power cycle 607 in which the UVLEDs are turned on for a set time, a purple indicator LED pulses throughout operation, and a feedback loop is run until completion. Within the feedback loop, the microcontroller tracks the temperature via the temperature sensor 608, UV dose via UV sensor 609, state of the magnetic lock 610, and the internal pressure via pressure sensor 611. If temperature decreases beyond a threshold within a 3 second timeframe OR UV dose drops below a set threshold OR the magnetic lock is unlocked at any point OR the pressure maintains or drops below atmospheric pressure within the first 5 seconds of operation, an operation error 604 will be triggered where all UVLEDs are powered off and a red indicator LED is flashed as a visual cue for the user. If the UV irradiation power cycle 607 is successfully completed, all LEDs will power off and a green indicator LED will power on until the operation switch is toggled again to release the magnetic lock.

Preferably, the internal control circuitry comprises a control switch for operation of the radiation source. Preferably, the internal control circuitry is adapted for monitoring the status of the apparatus. For example, indicate whether the apparatus is in sterilization mode (emitting radiation within the interior creating a risk if opened) and/or monitor the operations, "health" (e.g., whether diodes require replacing), performance (type and intensity of radiation, duration), etc. of the apparatus. Preferably, the internal control circuitry controls opening and closing the one or more openings by a mechanical or electronic switch. Preferably, the internal control circuitry controls locking the one or more openings through a mechanical or electronic locking mechanism. For example, when the user clicks an "open" button, the circuitry releases a lock allowing the "door" to open. Preferably, the internal control circuitry communicates with a toggle switch. Preferably, the internal control circuitry interfaces with a microcontroller that changes the state of a magnetic switch based on user input. Preferably, the internal control circuitry interfaces with a microcontroller that changes the state of a gear drive based on user input.

According to preferred embodiments, the apparatus further comprises one or more UV sensors (e.g., to detect the diode emissions) and/or one or more pressure sensors (e.g., to measure the pressure within the interior) and/or one or more humidity sensors (e.g., to measure within the interior) and/or one or more temperature sensors (e.g., to measure within the interior).

According to preferred embodiments, the apparatus further comprises one or more operational status indicators, such as colored LEDs or a LED display, to indicate the operational state of the apparatus.

According to preferred embodiments, the apparatus further comprises a transmitter and/or receiver for wireless communication protocols.

According to preferred embodiments, the apparatus further comprises a potting material encapsulating electronic components configured for UV protection, enhanced thermal management, and resistance to shock and vibration. Preferably, the potting material may be applied to one or more walls of the interior chamber to insulate the interior and exterior surfaces and enhance thermal dissipation (e.g., act as a heat sink). Preferably, applied to outer surface of walls or inner surface (e.g., contacting or exposed to interior. According to preferred embodiments, the potting material is within the volume between the housing and interior chamber to act as insulation. Preferably, at least one heat sink is affixed to or adjacent to the diodes. The heat sink is placed in such a way to not interfere with the diode emission. In one embodiment, the heat sink is placed on the external surface of the interior affixed to the non-emitting side of the diode. Preferably, at least one heat sink layer in thermal contact with one or more LEDs. Alternatively, a layer for each LED or each array of LEDs or at least one heat sink per side of interior.

Figure 7A:
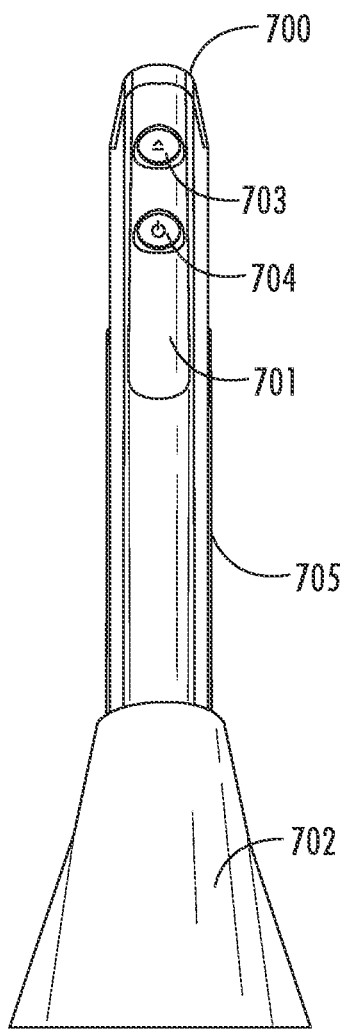
FIG. 7A is an external perspective front view of an illustrative embodiment of a charging dock system charging an apparatus according to one embodiment of the invention.
Figure 7B:
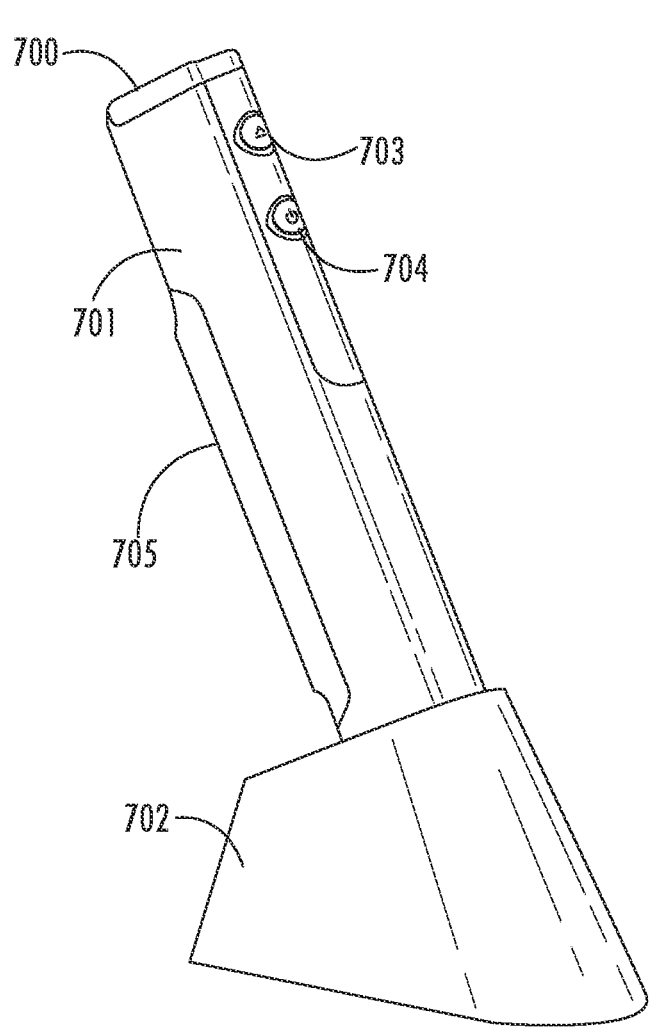
FIG. 7B is an external perspective side view of the system of FIG. 7A according to an embodiment of the invention.

According to preferred embodiments, the apparatus further comprises one or more EMI shielding components or layers to protect electronic components. According to preferred embodiments, power supply comprises at least one battery. Preferably, the battery is rechargeable. Preferably, the battery may be charged through a wall outlet. According to preferred embodiments, the battery may be charged by inserting the apparatus into a charging dock. Preferably, the apparatus is adapted to be inserted into the dock at an angle to ensure accessibility and visibility of the interior to wheelchair users. For example, FIGS. 7A and 7B show a system 700 including an apparatus 701 (including buttons 704 and 703 and grip 705) inserted into charging dock 702 according to one embodiment of the invention. The charging dock 702 connects to an external power supply, such as, but not limited to, a wall outlet (not shown). According to alternative preferred embodiments, the power source is powered using an external power source (e.g., may be powered or charged through wall outlet).

According to preferred embodiments, the apparatus, preferably the circuitry, further comprises memory storage. Preferably, the apparatus further comprises a serial code reader allowing serial numbers to be logged onto the memory storage. Preferably, a serial code reader allowing serial numbers to be transmitted via wireless communication protocols.

According to preferred embodiments, the battery is charged wirelessly (e.g., wireless charging). According to preferred embodiments, the battery is charged with a regenerative charging method such triboelectric generation or solar photovoltaic charging (e.g., regenerative battery).

According to preferred embodiments, the wireless transmitter transmits diagnostics in a HIPAA-compliant manner to relevant and authorized healthcare practitioners such as a primary care physician, urologist, occupational therapist, or registered nurse. Alternatively, the wireless transmitter transmits diagnostics to a telemedicine service (e.g., transmits diagnostics to urologist or telemedicine service). According to preferred embodiments, the wireless transmitter is able to transmit data to a central online repository to be viewed via a diagnostics dashboard. According to preferred embodiments, the wireless transmitter is able to transmit data to other local devices via near-field such as but not limited to RFID or wireless communication protocols such as but not limited to Bluetooth (e.g., transmit data to a diagnostics dashboard; communicates to other devices (Internet of Things—IoT)).

According to preferred embodiments, the apparatus further comprises one or more sensors to detect active and inactive cell population on a sampled point of the medical device before and after sterilization cycle is operated (e.g., cell detection method via camera or other sensor).

According to preferred embodiments, the apparatus further comprises an ultrasonic transducer (i.e., piezoelectric) used to transmit oscillatory ultrasonic waves into the interior. Ultrasonic waves are known as an effective tool to removing physical debris on solid surfaces and would be helpful in removing potential biofilm debris from the medical device before or during the sterilization cycle (e.g., ultrasonics).

Another embodiment of the invention relates to apparatus using radiation to sterilize but also including the use of reagents or fluids to optimize or enhance the sterilization process.

According to preferred embodiments, the further comprises a fluid adapted to enhance sterilization of the medical device. Preferably, the fluid is water. Preferably, the fluid contains hydrogen peroxide and/or contains silver particles.

Another embodiment of the invention further comprises a gel coated onto the interior and exterior surface of the medical device to enhance sterilization (e.g., a gel that enhances UV sterilization properties and sterilization methods). Preferably, the gel may also serve dual purposes as a sterilization enhancer and as a lubricant.

According to preferred embodiments, the apparatus is designed to be portable and easy to use by patients and/or caregivers. Specifically, the size, weight and overall design allows easy use. Preferably, the apparatus further comprises tabs and/or grips on the exterior of the apparatus to reduce slippage. Preferably, the apparatus further comprises a textured grip for the apparatus, even more preferably an ergonomic grip (e.g., configured to be gripped by a hand).

According to preferred embodiments, the apparatus is configured to be carried, stored and used. Preferably, the apparatus further comprises an exterior bumper guard to protect the apparatus from falls and shocks.

FIG. 8 shows a portable apparatus 800 according to one preferred embodiment having a total length 807, width 809, and thickness 808. Apparatus 800 includes 20 bumpers 803 at each end for drop protection. Indicator light 802 is depicted along one edge, with textured grip 805, slippage grip 806, and operational button 804 on opposite side. Apparatus 800 has an opening 801 (shown as closed in FIG. 8) controlled with switch 804. The length of the opening cap 810 is smaller than the length of the body 811. Preferably, the apparatus further comprises a carrying sleeve with one or more cavities for holding medical supplies and/or cleaning supplies (preferably, disposable medical supplies). Preferably, the apparatus further comprises a holster adapted to allow the apparatus to be carried by a person and/or without the use of their hands by mounting onto an object such as a wheelchair or table.

Figure 5:
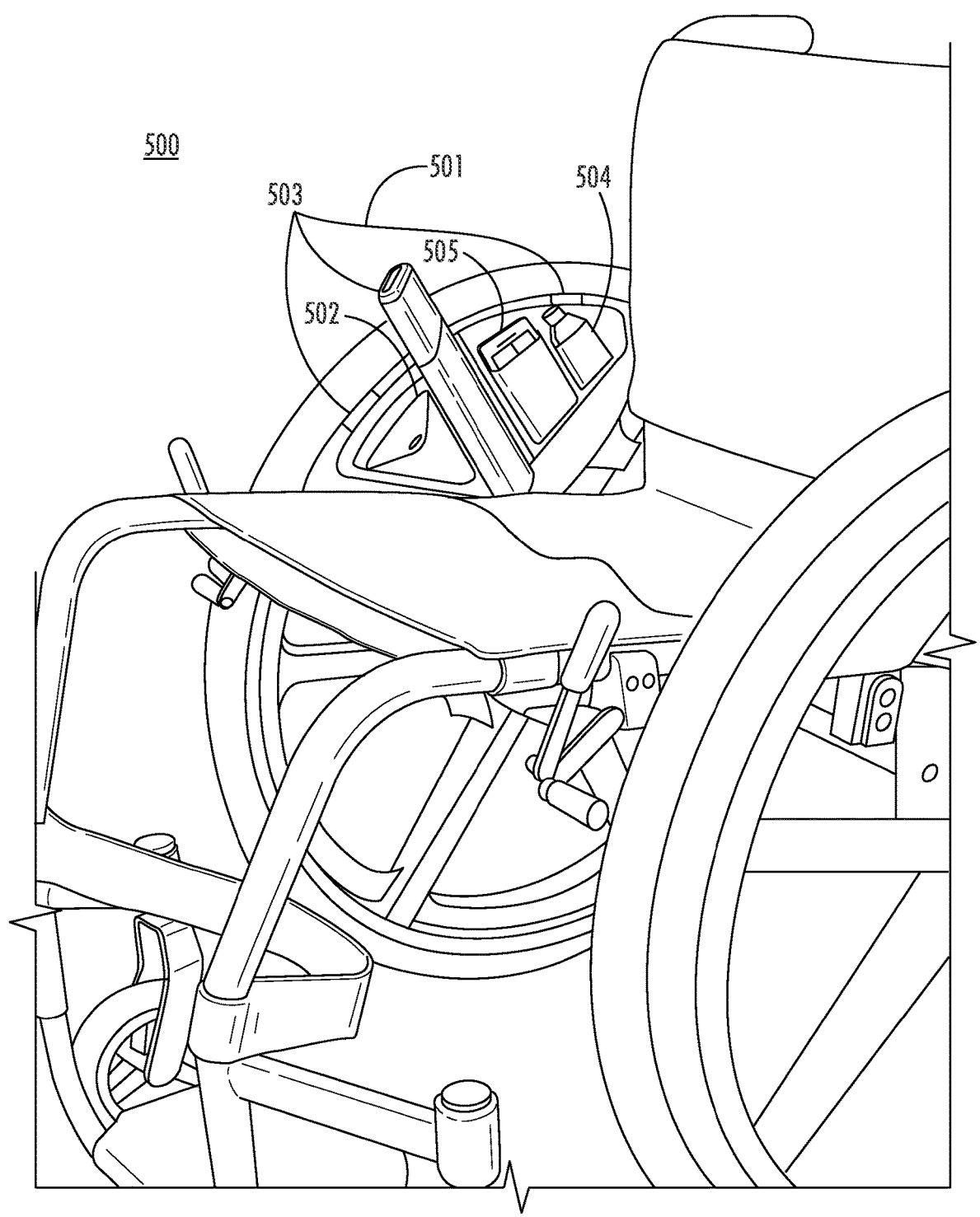
FIG. 5 is an external perspective side view of an illustrative embodiment of an apparatus held in an illustrative embodiment of a holster system attached to a wheelchair.

An isometric view of a system according to one preferred embodiment is depicted in FIG. 5. The holster system 500 comprises a sterilization apparatus 501 and holster 502. The holster 502, a shown, has several pockets that may be opened or closed that allow insertion of the sterilization apparatus to be carried without the use of hands. A clip 503 affixed to the holster allows the holster to be clipped onto the frame of a wheelchair. According to further preferred embodiment, the holster would include buckles and straps instead of a clip (e.g., to attached to a user's belt). Preferably a container with medical or cleaning supplies 504 is also carried within one or more of the holster pockets. Preferred embodiments may carry sterile gloves, water-based lubrication, isopropyl alcohol, or betadine. A remote control (in this embodiment, a user's smartphone) 505 is used to monitor and control operation of the sterilization apparatus via wireless communication.

According to preferred embodiments, the apparatus is adapted to be operated through a remote control. Preferably, the remote control is a cellular device (e.g., a smartphone). Preferably, the remote control is a personal computer. Preferably, the apparatus includes personal identification information such as but not limited to name, address, phone number, preferably labeled on the exterior of the apparatus.

According to preferred embodiments, text and/or visual instructions and/or personal identification information are labeled on the exterior or interior of the apparatus. For example, an arrow or a number near a stub to put the catheter port into (e.g., to position a catheter consistently), not intending for much text, if any, on the interior. An illustrative example is depicted as 209 in FIG. 2. Preferably, text and/or visual instructions are labeled on the exterior or interior of the carrying sleeve.

According to preferred embodiments, the apparatus further comprises a removable introducer tip for catheters, as shown as tip 403 in FIG. 4. Preferably, the introducer tip is made of UV transparent material or composite. Preferably, the introducer tip is made of microwave transparent material or composite such as polyethylene. Preferably, the introducer tip is made of heat resistant material such as silicone.

The apparatus further includes an opening or aperture in at least one wall or an entire wall that is capable of opening to allow placement of the target medical device within the interior chamber. The chamber so configured allows for the removable placement of the target device (e.g., catheter) into and out of the interior chamber of the apparatus. In preferred embodiments, the medical device is a catheter with one part in 5 vivo (e.g., as shown as 404 in FIG. 4) and one part ex vivo (e.g., as shown as 405 in FIG. 4).

According to one embodiment of the present invention, one or more of the light sources may include a ball or hemispherical lens system for optimal launch of UV light within the interior and/or a UV transparent optical window for separating the chamber 10 interior from the LED (e.g., as shown in FIG. 3).

According to one embodiment of the present invention, a support affixed to one or more walls may be included, allowing the target medical device to be suspended or positioned or held in place consistently such that the light source and support(s) allow all surfaces of the target device to be exposed to substantial and uniform UV irradiation.

According to one embodiment of the present invention, the apparatus contains a sealing device for the opening such as a gasket or an O-bearing to prevent leakage of environmental fluids from contaminating the medical device.

According to one embodiment of the present invention, the power supply may be portable (e.g., a battery), may be internally housed, and, preferably, may be rechargeable. The power supply provides energy to the LEDs such that the LEDs emit UV radiation into the interior. In preferred embodiments, the apparatus is adapted to be connected to an external power source via power cord (e.g., from a wall outlet) or docking station (e.g., a power cord).

According to one embodiment of the present invention, the apparatus contains internal control circuitry such as an Arduino microcontroller. Preferably, the control circuitry is configured and used to control operation of the radiation source. Preferably, the control circuitry communicates with a network of switches and locks to enable the user to open and close the apparatus. Preferably the lock may be a mechanical mechanism such as a gear drive or an electronic mechanism such as a magnetic lock.

Furthermore, according to preferred embodiments of the present invention, the apparatus contains a number of sensors to detect environmental conditions such as UV, pressure, humidity, and temperature. These sensors are used to detect any abnormalities in normal operation and feedback to an automatic locking system when the radiation source is emitting. An illustrative operating protocol is depicted in FIG. 6.

According to one embodiment of the present invention, the apparatus further comprises a textured grip to provide an ergonomic handle, allowing safer handling of the apparatus. According to one embodiment of the present invention, the apparatus housing further comprises one or more legs or supports or tabs or grips on the exterior surface of the housing to allow the unit to stand upright and in a stable manner. According to one embodiment of the present invention, the apparatus further comprises an exterior bumper guard around the housing to protect the apparatus from falls and shocks.

According to one embodiment of the present invention, the apparatus further comprises one or more cavities with one or more openings intended for holding disposable medical or cleaning supplies such as sterile gloves, lubricant, and betadine. An example is illustrated in FIGS. 1A and 1B. According to one embodiment of the present invention, the apparatus is adapted to be placed in an external holster, intended to be carried by a person or mounted onto an object such as a wheelchair. An example is illustrated in FIG. 5.

According to one embodiment of the present invention, the apparatus is further adapted to have one or more components to be modular, allow maintenance and replacement by users or qualified technician (e.g., allow for maintenance and replacement of diodes or frame or any part of apparatus).

According to one embodiment of the present invention, the apparatus further comprises text and/or visual instructions on one or more of the exterior surfaces of the housing or one or more of the interior surfaces of the interior chamber. The instructions are intended to allow users to easily grasp the correct procedure with minimal training and experience. An example of instruction would be a bubbled number to indicate the step number along with an arrow pointing to a switch. An example is illustrated in FIG. 2. For example, description in text and/or visual instructions, arrows or bubbled number on interior.

Another aspect of the invention relates to methods of sterilizing one or more medical devices or other products using radiation. Preferably, method of sterilizing and sealing a medical device or other product in a portable enclosure. The method preferably comprises sealing a medical device within a sterilization chamber comprising a plurality of radiation emitting diodes such that the diodes emit radiation into the chamber and the radiation is confined to the interior enclosure and irradiates the surfaces of the medical device, for a predetermined period of time defining a sterilization cycle, deactivating pathogenic biological contaminants that may be present on the medical device.

One embodiment of the invention relates to a method for sterilizing a medical device using ultraviolet radiation comprising: (a) enclosing the medical device in a chamber; (b) sealing the chamber; and (c) irradiating surfaces of the medical device with UV radiation thereby destroying biological contaminants on the surfaces of the medical device. Another embodiment of the invention relates to a method for sterilizing a medical device using microwave radiation comprising: (a) enclosing the medical device in a chamber; (b) sealing the chamber; and (c) irradiating surfaces of the medical device with microwave radiation thereby destroying biological contaminants on the surfaces of the medical device. Another embodiment of the invention relates to a method for sterilizing a medical device using thermal radiation comprising: (a) enclosing the medical device in a chamber; (b) sealing the chamber; and (c) irradiating surfaces of the medical device with thermal radiation thereby destroying biological contaminants on the surfaces of the medical device.

According to preferred embodiments, the radiation is generated using UV-C LEDs. Preferably, the LEDs are automatically switched off due to a sensor event trigger. For example, the opening is opened or the power supply is insufficient, etc. Preferably, the method further comprises cleaning the medical device prior to the step of irradiating. Preferably, further comprising chemically or otherwise cleaning the medical device within the chamber. More preferred, the cleaning entails using a fluid such as water or isopropyl alcohol to be applied to the interior surface and then removing the fluid along with contaminants by wiping with a clean and sterile towel, towelette, abrasive brush, or equivalent. According to preferred embodiments, the method further comprises additional irradiation pulse cycling steps after the irradiating.

According to preferred embodiments, the method further comprises removing the medical device from the chamber, utilizing the medical device in vivo and repeating the method of enclosing and irradiating, preferably without damaging the medical device. In this way, the medical device may be used for repeated cycles without loss of intended functional properties. Preferably, the medical device is a catheter comprising an ex-vivo portion and an in vivo portion.

According to preferred embodiments, the method further comprises using a fluid added to the chamber to enhance UV sterilization. Preferably, the fluid comprises one or more components selected from the group consisting of water, hydrogen peroxide, and silver particles.

According to preferred embodiments, the method further comprises maintenance cleaning of the sterilization chamber using a cleaning solution (preferably isopropyl alcohol) after the sterilization.

According to preferred embodiments, the method further comprises recharging the apparatus using a charging dock, as depicted in FIGS. 7A and 7B. According to preferred embodiments, the method further comprises downloading data from the apparatus to an external device. In preferred embodiments, an additional step to clean product exterior with an agent such as water or isopropyl alcohol is used. In further preferred embodiments, an additional step to clean interior of apparatus sterilization chamber with an agent such as water or isopropyl is used. In other preferred embodiments, the radiation is able to inactivate microorganisms in a manner that does not damage the inserted medical device.

According to preferred embodiments, the method further comprises cleaning apparatus exterior using a cleaning solution (preferably isopropyl alcohol) after the sterilization. Preferably, the method further includes cleansing the medical device in water or other solution prior to the step of irradiating. Event indicators of environmental breach or contamination during the sterilization cycle may be used to stop irradiation to avoid accidental human UV exposure. Preferably, the method is repeated to sterilize the same medical device (e.g. catheter) or other device(s), preferably multiple times.

According to preferred embodiments, the apparatus is configured to be used in a system with at least one medical device, preferably an intermittent catheter. Preferably, the medical device is used in common everyday use environments such as outdoors, or in a home, or at work, or while traveling. Preferably, the medical device is adapted for insertion into a patient. Preferably, the medical device is adapted to be used by a patient. Preferably, the medical device is CLIA waived. Preferably, the medical device is adapted for home use. Preferably, the medical device is a plastic, more preferably consists essentially of plastic. Preferably, the medical device takes the form of a tube, preferably a flexible tube. In one preferred embodiment, the medical device consists essentially of a material or composite transparent to radiation emitted from apparatus radiation source. In preferred embodiments, the medical device consists essentially of a flexible material, more preferably the medical device consists of a flexible material or is flexible.

Another embodiment relates to a method for sterilizing a medical device using different types of radiation. Preferably, the types of radiation are UV radiation, microwave radiation, and thermal radiation. Preferably, the methods comprise enclosing a medical device in a chamber, sealing the chamber, and irradiating surfaces of the medical device with radiation thereby destroying active biological contaminants on the surface of the medical device.

In preferred embodiment, the radiation is generated via UVLEDs wherein preferably the UVCLEDs will automatically switch off by a sensor event trigger as previously illustrated in flowchart shown in FIG. 6.

In preferred embodiments, the method further comprises cleaning the exterior device with a cleaning agent such as water or isopropyl alcohol.

In preferred embodiments, the method further comprises cleaning the interior of the apparatus with a cleaning agent or mixture of cleaning agents including but not limited to water, hydrogen peroxide, and/or silver particles. Preferably, the sterilization is repeatable on a medical device and does not damage the medical device in such a way to alter its intended functionality.

In preferred embodiments, the method further comprises additional pulsed cycling radiation as it has been noted in academic literature that repeated sterilizations can provide a potentially more effective sterilization method than fixed output.

In preferred embodiments, the method further comprises the use of a fluid to enhance sterilization properties of the apparatus. Preferably, the fluid comprises a combination of water, hydrogen peroxide, and/or silver particles as all three have been noted in literature to enhance sterilization.

In preferred embodiments, the method further comprises using a charging dock to recharge the sterilization apparatus power supply.

In preferred embodiments, the method further comprises downloading data from the sterilization apparatus to an external device (e.g., a thumbdrive, a smartphone, laptop or other computer system). Preferably, the operational history is stored on local memory in the sterilization apparatus to be transmitted (via cable or wireless) to a computer or cellphone for a user or healthcare practitioner to monitor.

In preferred embodiments, the method further comprises coating the interior and/or exterior surfaces of the medical device with a gel to enhance sterilization prior to sterilization (e.g., a gel that enhances UV sterilization properties). Preferably, this method further comprises removing the gel (e.g., by cleaning).

Another aspect of the invention relates to a system comprising at least one apparatus as described herein for sterilization of medical products and one or more additional components or devices to facilitate the convenient sterilization of one or more medical products using radiation. Preferably, the system is adapted for use by a patient. Preferably, the system is CLIA waived. Preferably, the system is adapted for home use. Preferably, the medical device is a medical device for use in common everyday use environments such as outdoors or in a home. Preferably, the medical device is adapted for insertion into a patient. Preferably, the medical device is adapted to be used by the patient and/or is CLIA waived and/or is adapted for home use. Preferably, the medical device comprises plastic or glass, even more preferably consists essentially of plastic or glass. Preferably, the medical device comprises a tube, preferably a plastic tube.

According to one preferred embodiment, the system comprises a container (e.g., bag, carrier, case) and the system (including components) can be enclosed in the container. Preferably, the container can be carrier by a patient. Preferably, the largest dimension of the container is less than two feet and weight less than 10 lbs.

According to another embodiment, the system further comprises a remote control for remote operation and monitoring the apparatus operational status such as determining whether the apparatus is on or off and determining whether the sterilization cycle was completed or not yet started. According to a preferred embodiment, the remote control is a cellular device or a personal computer. Another embodiment of the invention relates to a system comprising an apparatus and at least one medical device.

According to one preferred embodiment, the system further comprises a remote control. Preferably, the remote control is a cellular device and/or a personal computer.

According to one preferred embodiment, the system further comprises a holster for the apparatus. Preferably, the holster has straps and/or buckles and/or clips to allow mounting the apparatus to objects. Preferably, the holster has one or more openings that can be opened or closed.

According to one preferred embodiment, the system further comprises a container for holding the medical device to protect the medical device from contact contamination after removal from the interior within the apparatus, wherein the container is proportionally sized to enclose the medical device inside the interior. Preferably, the container is a tube or is a bag or is a box. Preferably, the container is made of polyurethane, silicone, fluoropolymer (ex. PTFE, FEP, PVDF), and/or composite.

According to preferred embodiments, the container has an opening for the medical device. Preferably, the opening can open and close. According to preferred embodiments, the system comprises the apparatus and a carrying case for the apparatus. According to preferred embodiments, the system comprises the apparatus and at least one container containing cleaning solution.

According to preferred embodiments, the system comprises the apparatus and a remote control for operating the apparatus. According to preferred embodiments, the system comprises the apparatus and a set of instructions for operating the apparatus. According to preferred embodiments, the system comprises the apparatus and a charging cable for charging the apparatus. According to preferred embodiments, the system comprises the apparatus and a charging dock for recharging the apparatus.

According to another embodiment, the system comprises at least one apparatus, a medical device, and a holster for which the apparatus was adapted. This system is intended to allow a user to carry the apparatus without use of their hands. One preferred embodiment of the holster includes strap and/or buckles to allow the user to mount onto a fixed object such as a wheelchair or around the user's shoulders and torso.

One preferred embodiment of the holster includes one or more openings that may be opened or closed to allow insertion of the apparatus and additional items the user may carry. Additionally, these holes may function as a tether for a rope to cinch and close the holster, or carabiner to hang or carry the holster.

According to another embodiment, the system further comprises a container to protect the medical device from contact contamination after removing the device from the interior of the apparatus. An additional function of this container is to guide and improve consistent placement of said medical device. This container is proportionally sized to the medical device to enclose said device and fit within said apparatus interior. According to an embodiment of the container, it may take the form of a tube, bag, or box. An example is depicted in FIG. 4. According to another embodiment of the container, the container is made of polyurethane, silicone, fluoropolymer, or composite material. In a preferred embodiment, the container is transparent to the radiation emitted from apparatus radiation source or sources. In a preferred embodiment, the container has an opening that can open and close for insertion of said medical device.

According to an embodiment of the claimed system, the system further comprises a fluid to be used to enhance UV sterilization, preferably, a fluid in one or more containers. Preferably, the fluid comprises one or more components selected from the group consisting of water, hydrogen peroxide, and silver particles. Preferably, the fluid is contained in a separate container. Preferably, the fluid container is housed in one of the apparatus cavities (e.g., the apparatus includes a cavity to fill with the fluid).

Another embodiment of the system according to the invention further comprises a gel used to coat the interior and exterior surface of the medical device to enhance sterilization.

According to preferred embodiments, the system further comprises a charging dock for recharging the apparatus. Preferably, the charging dock is designed such that the apparatus is inserted at an angle, as depicted in FIGS. 7A and 7B. For example, this allows users who are seated (such as wheelchair bound users) to more easily access the dock and inspect the interior when the apparatus is opened.

As exemplified, the apparatus may include any chamber having diodes which emit radiation to sterilize targeted surfaces of medical devices. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

According to alternative aspects of the invention, the methods and systems described above can be configured or adapted to sterilize other products (e.g., cooking devices, eating utensils, surgical instruments, medical implants, contact lenses, manufacturing equipment components used for biological/pharmaceutical manufacturing or food production). That is, the invention described above can be used to sterilize any component having a surface requiring sterilization.

FIGS. 10-14 illustrate another embodiment of methods and systems for urinary catheterization, urinary catheter sterilization, and combined data acquisition and deposition. Specifically, FIGS. 10-14 illustrate an at-home sterilization and data acquisition and deposition device including a housing having an opening or series of openings for receiving up to six medical devices, a sterilization chamber formed within the housing that is lined with sterilizing radiation reflecting material, and several sources of sterilizing radiation disposed within the sterilization chamber for sufficient emission of radiation to achieve a significant log reduction of any pathogens present on the medical devices, and an RFID scanner and sensor suite configured into the housing that prevents sterilization of non-system components, radiation emission into the environment, and that can pair with a user's mobile device. An individual catheterization system includes an at-home sterilization and data acquisition device, a software-enabled analysis of data acquired through the system, a set of accessories to enable proper lubrication, cleaning, and radiation-based sterilization of medical devices, and a set of RFID-enabled medical devices designed to facilitate sterile emptying of the bladder by providing a tactile interface that prevents direct contact between the individual and the parts of the medical devices that enter the individual's body.

Intermittent urinary catheters are essential medical devices that are typically used by individuals with neurogenic bladder and lower urinary tract symptoms to manually empty the bladder of urine if it is neurologically or physically obstructed. While the use of these catheters is oftentimes considered to be the healthiest short- or long-term method for bladder management, especially when compared to alternatives like suprapubic or indwelling catheters, improper use of these catheters can result in contact contamination of the catheter, the subsequent introduction of pathogens to the bladder, and an overall substantially higher urinary tract infection [UTI] risk for the individual. Additionally, improper use of the catheter is extremely likely given the overall lack of ergonomic consideration in the design of the catheter in the case of standard, low-cost catheters. While easier-to-use catheters do exist, they do so at a price point that is often 5-7× the price of standard, low-cost catheters. Insurance coverage of these easier-to-use catheters is limited, and reuse is prevalent to offset the financial cost to the individual. Moreover, compliance with clean catheterization guidelines is generally low due to their onerous nature and requirement of a vast kit of parts that are difficult, if not impossible, to transport.

A need exists for an easy-to-use and affordable catheterization system that mitigates the UTI risk associated with the use of today's catheters.

Figure 10:
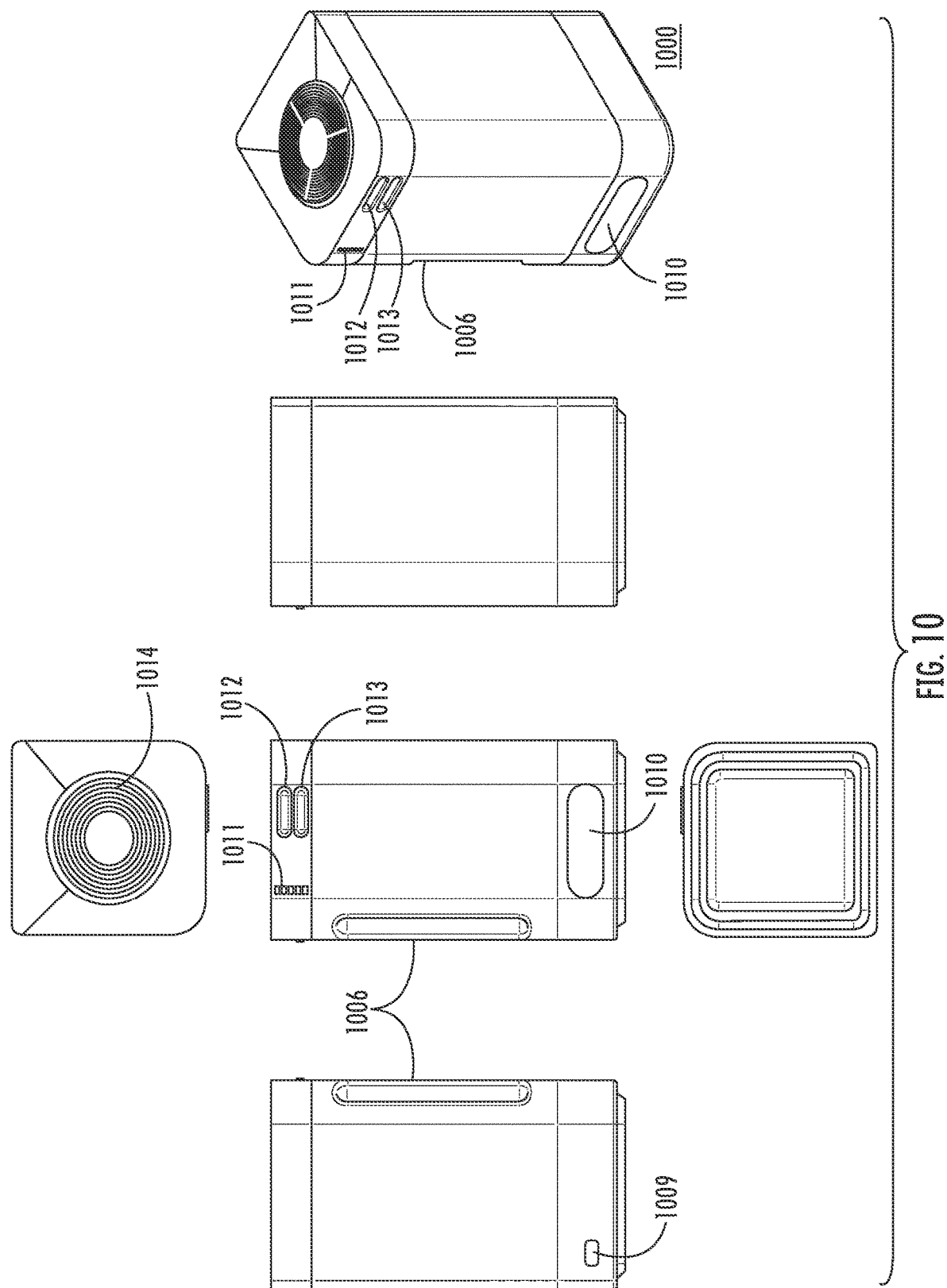
FIG. 10 includes various views of an illustrative embodiment of the apparatus, featuring a front, left, right, top, bottom, and isometric view.
Figure 11:
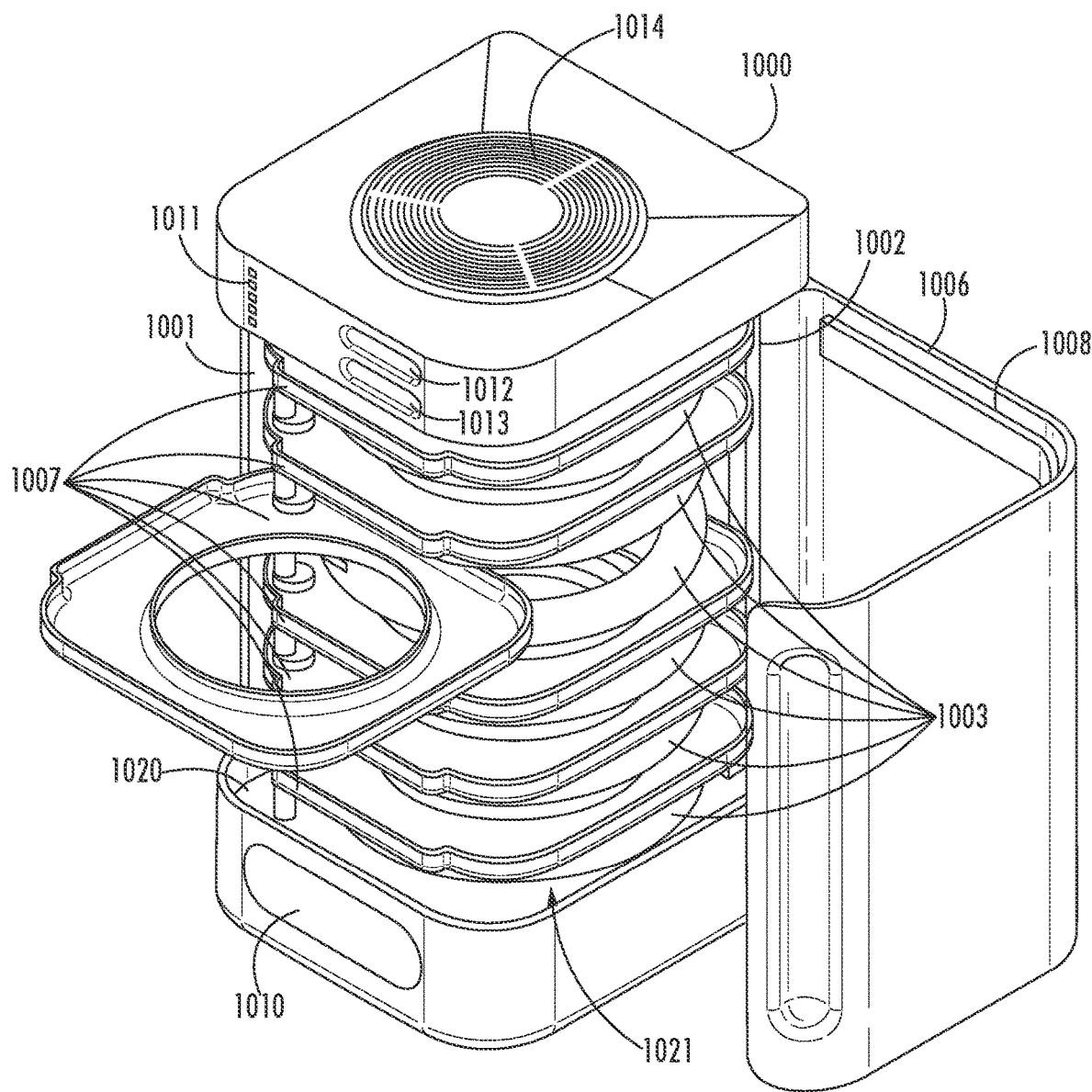
FIG. 11 is an isometric view of an illustrative embodiment of the apparatus with the door open and an individualized tray, specially adapted to receive a medical device, pivoted outwards.
Figure 12:
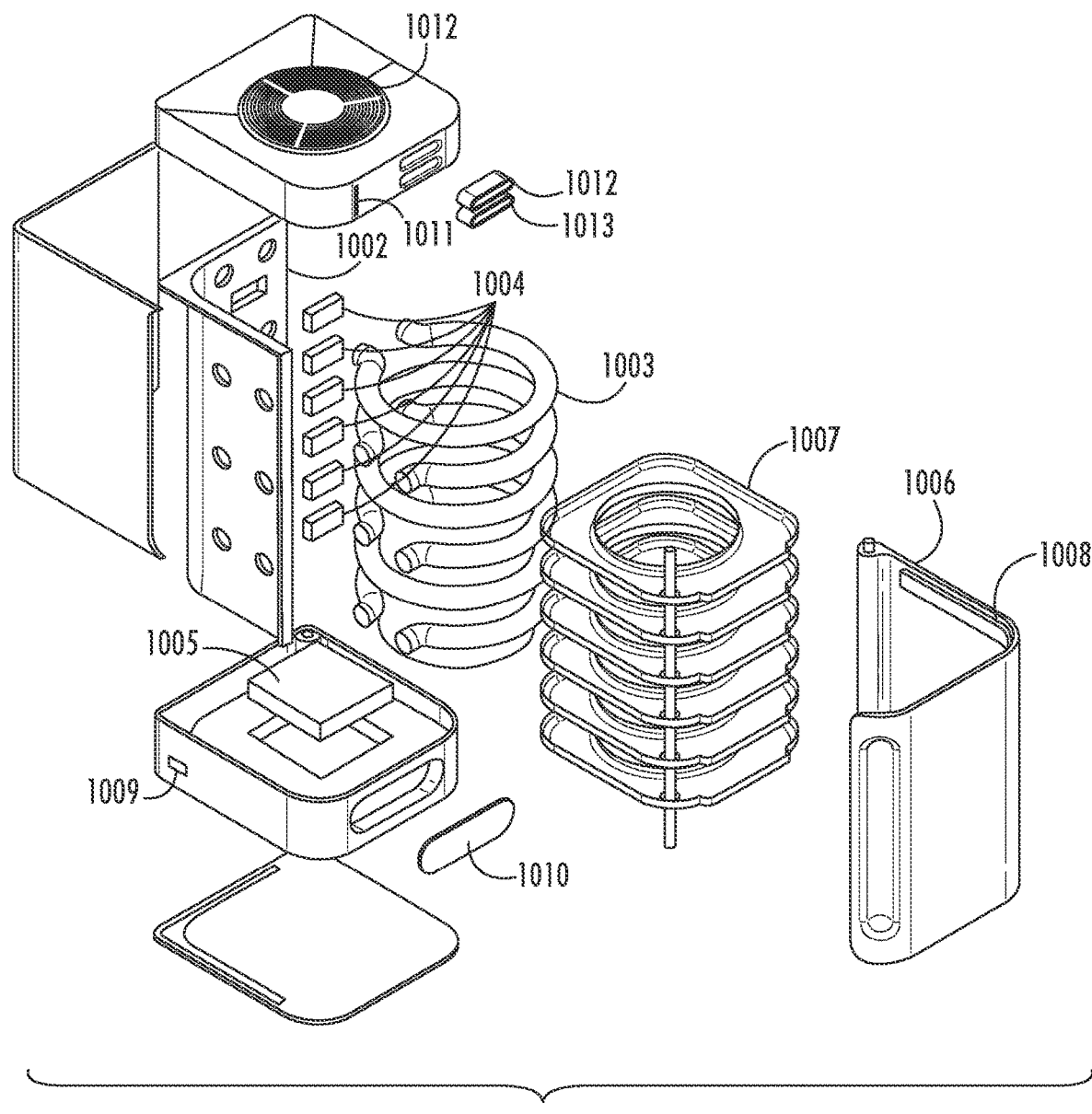
FIG. 12 is an isometric exploded view of an illustrative embodiment of the apparatus.

Specifically, as illustrated in FIGS. 10-12, a low-footprint sterilizer 1000 may sterilize up to six catheters 1100, 1200 and insertion aids 1106, 1206 simultaneously using UVC-bulbs 1003. Each catheter 1100, 1200 and insertion aid 1106, 1206 may be sandwiched by the UVC bulbs 1003 to facilitate adequate log reduction/sterilization of the catheter 1100, 1200 between uses. The catheters 1100, 1200 and insertion aids 1106, 1206 may each fit into an individualized tray 1007 within the unit 1000. Alternatively, the catheters 1100, 1200 and insertion aids 1106, 1206 may be placed into resealable UVC-transparent plastic bags to facilitate their sterile transport after removal from the sterilizer 1000 after the completion of a sterilization cycle. Specifically, an at-home sterilization and data acquisition and deposition device 1000 including a housing 1020 having an opening or series of openings 1001 for receiving up to six medical devices 1100, 1200, a sterilization chamber 1021 formed within the housing 1020 that is lined with sterilizing radiation reflecting material 1002, and several sources of sterilizing radiation 1003 disposed within the sterilization chamber 1021 for sufficient emission of radiation to achieve a significant log reduction of any pathogens present on the medical devices 1100, 1200, and an RFID scanner 1004 and sensor suite 1005 configured into the housing 1020 that prevents sterilization of non-system components, radiation emission into the environment, and that can pair with a user's mobile device.

In accordance with other aspects of the present invention, the opening of the device housing 1020 consists of a two-panel door 1006 that swings clear of the opening to facilitate easy access to the sterilization chamber 1021 housed within, which in turn features individualized trays 1007 specially configured to hold individual medical devices 1100, 1200 for sterilization. These trays 1007 can be individually rotated outwards to expose their contents for removal, access, and deposit as seen in FIG. 11. In accordance with yet other aspects of the present invention, the door 1006 used to access the interior of the device 1000 comprises one quarter to one half of the overall surface of the device 1000 such that the user has greater accessibility to the individual trays 1007 when the device 1000 is open and will be able to remove or deposit medical devices 1100, 1200 more easily than a lid comprising only the front wall of the device 1000. In accordance with yet other aspects of the present invention, the door 1006 used to access the interior of the device 1000 may feature an embedded sealing gasket 1008 along the outer perimeter of the door 1006 that forms a hermetic seal with the walls of the sterilization device 1000 when closed, such that it is non-permeable by gas or liquid. In accordance with yet other aspects of the present invention, the closing of the door 1006 may initiate the beginning of a sterilization cycle provided that other requirements for the initiation of a sterilization cycle are met.

In accordance with other aspects of the present invention, the sterilization chamber 1021 formed within the housing 1020 may be lined with a sterilizing radiation reflecting material 1002 such as mirrored aluminum or PTFE to provide high reflection of any sterilization radiation that is not absorbed or otherwise attenuated by the medical devices housed within the device 1000.

In accordance with other aspects of the present invention, the source of the sterilization radiation 1003 for the at-home sterilization and data acquisition and deposition device 1000 consists of several low voltage UV emitters that produce one primary ultraviolet wavelength [253.7 nm, 275 nm, 280 nm, or 285 nm] for the purposes of disinfection and sterilization. In a preferred embodiment of the present invention, the UV emitters 1003 are further defined as UV mercury-based lamps. In accordance with other aspects of the invention, these lamps are housed in individual quartz envelopes with a Teflon-based coating to provide shatter-resistant properties to the lamp housing 1020. In another preferred embodiment of the present invention, the UV emitters 1003 are further defined as UV light emitting diodes as described above and illustrated in at least FIG. 1.

In accordance with other aspects of the present invention, the at-home sterilization and data acquisition and deposition device 1000 includes one or more RFID modules 1004 that verify the authenticity of all medical devices 1100, 1200 placed within the device 1000 for sterilization through the scanning of RFID chips 1101, 1201 embedded in all of the aforementioned medical devices 1100, 1200 and writes information to the individual chips 1101, 1201 in accordance with the number of times that the at-home sterilization and data acquisition and deposition device 1000 has been used to sterilize the medical devices 1100, 1200. The RFID module 1004 may electronically interface with the microcontroller and/or logic board that controls the emission of sterilization radiation into the interior chamber 1021 of the device 1000 for sterilization to prevent the emission of sterilization radiation if an individual has placed a RFID-embedded medical device 1100, 1200 that has been sterilized more than a pre-specified number of times. The RFID module 1004 may also electronically interface with a suite of sensors 1005 through a microcontroller and/or logic board to ascertain whether or not a medical device 1100, 1200 lacking an RFID 1101, 1201 has been inserted into the at-home sterilization and data acquisition and deposition device 1000, and the microcontroller may prevent the emission of radiation sterilization until the medical device 1000 lacking an RFID has been removed from the at-home sterilization and data acquisition and deposition device 1000.

In accordance with other aspects of the present invention, the at-home sterilization and data acquisition and deposition device 1000 may include a safety interlock mechanism. The safety interlock mechanism may consist of a Hall Effect sensor and a rare earth magnet, and wherein the Hall Effect sensor senses the magnetic field of the magnet when the access door 1006 is closed and sends a signal to the user interface indicating a ready state for the excitation of the radiation source 1006. The sterilizer circuit and microcontroller logic may utilize a sensor suite that includes but is not limited to hall effect, temperature, and pressure sensors to validate that the sterilizer is completely closed for the duration of the sterilization cycle, to prevent UVC radiation from escaping the sterilization unit. In accordance with yet other aspects of the present invention, the at-home sterilization and data acquisition and deposition device 1000 may include an electronic safety mechanism. The electronic safety mechanism may consist of a suite of sensors 1005 that detect ambient temperature, light, and pressure within the sterilization chamber 1021, and transmits a signal to interrupt any on-going sterilization cycle upon detection of a dramatic change in readings throughout the course of the cycle. In accordance with yet other aspects of the present invention, the at-home sterilization and data acquisition and deposition device 1000 may include a feedback loop that consists of a radiation sensor or suite of sensors placed in a hard-to-irradiate location within the sterilization chamber 1021, wherein the sterilization cycle continues so long as the sensor or suite of sensors has not registered sufficient radiation to kill pathogens that cause UTIs. In accordance with yet other aspects of the present invention, the at-home sterilization and data acquisition and deposition device 1000 may include a feedback loop that incorporates one or more sensors to detect active and inactive cell population on a sampled point of the medical device 1100, 1200 before and after sterilization cycle is operated (e.g., cell detection method via camera or other sensor).

In accordance with other aspects of the present invention, the at-home sterilization and data acquisition and deposition device 1000 may use an ultrasonic transducer (i.e., piezoelectric) used to transmit oscillatory ultrasonic waves into the interior of the sterilization chamber 1021. Ultrasonic waves are known as an effective tool to removing physical debris on solid surfaces and would be helpful in removing potential biofilm debris from the medical device 1100, 1200 before or during the sterilization cycle (e.g., ultrasonics).

In accordance with other aspects of the present invention, a micro fluid pump is used to pump fluid into and out of the at-home sterilization and data acquisition and deposition device 1000. In this embodiment, the fluid pump is used to pump a mixture of water, hydrogen peroxide, and silver particles to enhance sterilization. It is known that hydrogen peroxide and silver particles enhance DNA inactivation when using in conjunction with UV radiation. After sterilization, the micro fluid pump will remove remaining fluid within the sterilization chamber 1021. The micro fluid pump can either be included within a unit that is attached to the apparatus or integrated within the sterilizer device 1000. For example, the sterilizer device 1000 may have a port to connect to a fluid pump to provide fluid to the interior chamber 1021.

In accordance with other aspects of the present invention, the at-home sterilization and data acquisition and deposition device 1000 further comprises one or more EMI shielding components or layers to protect electronic components. According to preferred embodiments, the power supply comprises at least one adapter 1009 configured to interface with and receive power from a standard wall outlet.

In accordance with other aspects of the present invention, the at-home sterilization and data acquisition and deposition device 1000 may pair with an individual's mobile phone or personal computer or other such device to deliver usage statistics, detailed troubleshooting steps, status updates, as well as other data. This pairing may be further defined as enabling an individual to scan the RFID-embedded medical devices 1100, 1200 to verify their authenticity as well as observe the remaining number of sterilizations possible for the scanned devices 1100, 1200. This pairing may be further defined as enabling an individual to remotely control the at-home sterilization device 1000 through their mobile phone or personal computer or other such device.

In accordance with other aspects of the present invention, the at-home sterilization and data acquisition and deposition device 1000 may be configured to have a screen 1010 on the device 1000 in order to communicate to an individual using the device 1000 the current status of a sterilization cycle, or otherwise indicate the remaining longevity of the RFID-embedded medical devices 1100, 1200 that are being used in conjunction with and are being sterilized by the at-home sterilization device 1000. The remaining longevity of the RFID-embedded medical devices 1100, 1200 may additionally be communicated to an individual via RGB LEDs 1011 corresponding to each individual medical device 1100, 1200 located on the front face of the at-home sterilization device 1000.

In accordance with other aspects of the present invention, the at-home sterilization and data acquisition and deposition device 1000 may initiate a sterilization cycle when an individual presses a start button 1012 located on the front face of the at-home sterilization device 1000, and may prematurely end a sterilization when an individual presses a stop button 1013 located on the front face of the device 1000.

In accordance with other aspects of the present invention, the at-home sterilization and data acquisition and deposition device 1000 may be configured to vent heat generated from the electrical components and radiation emission sources held within through a series of vents 1014 located on the top of the device 1000.

In accordance with other aspects of the present invention, the at-home sterilization and data acquisition and deposition device 1000 may be configured to be battery-powered and portable. This device 1000 may pair with one or many at-home sterilization and data acquisition devices to accurately track medical device 1100, 1200 usage and frequency.

Figure 13:
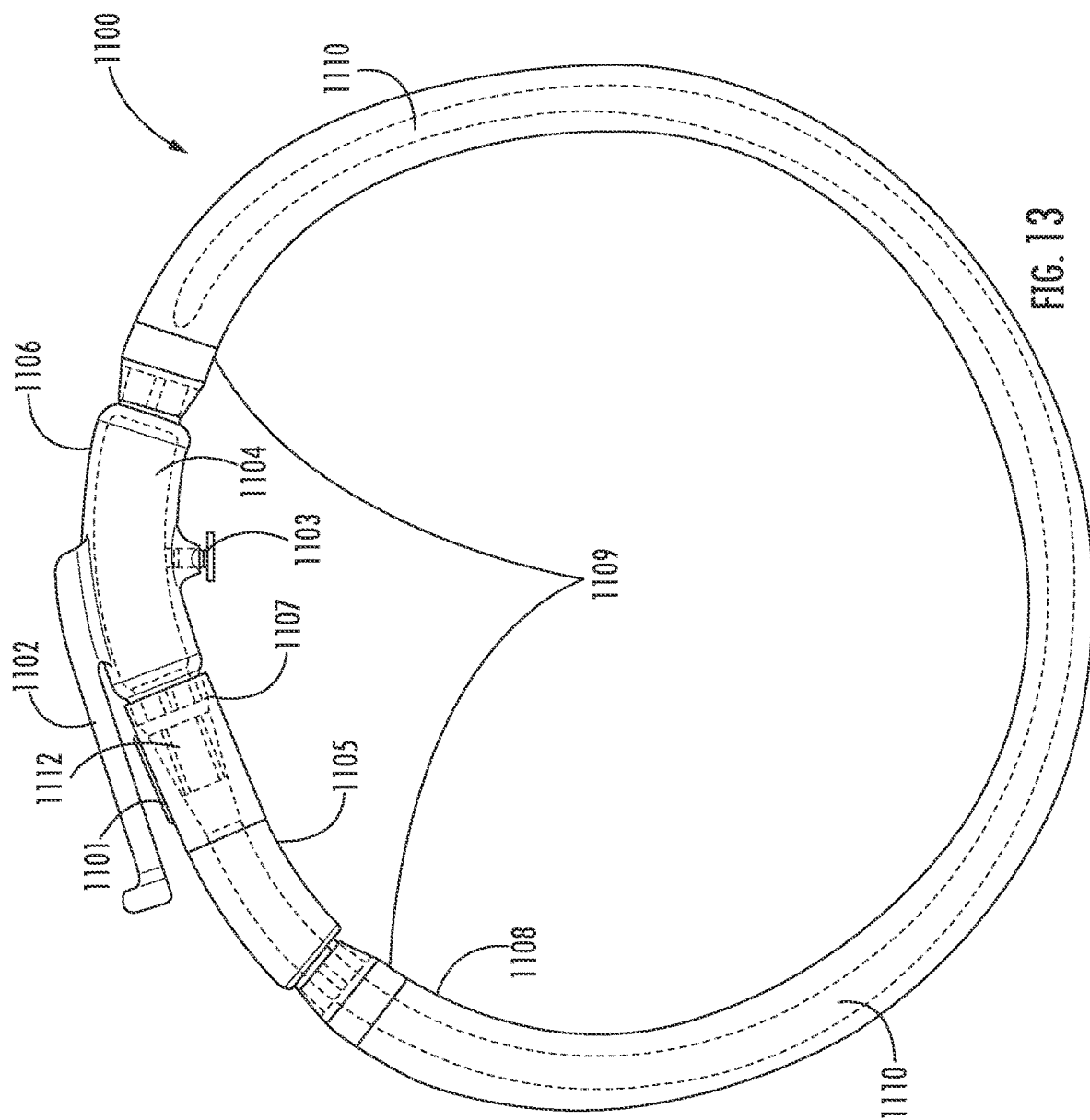
FIG. 13 is a side view of an illustrative embodiment of an RFID-tagged medical device specially adapted for use by males for the purposes of urinary catheterization.
Figure 14:
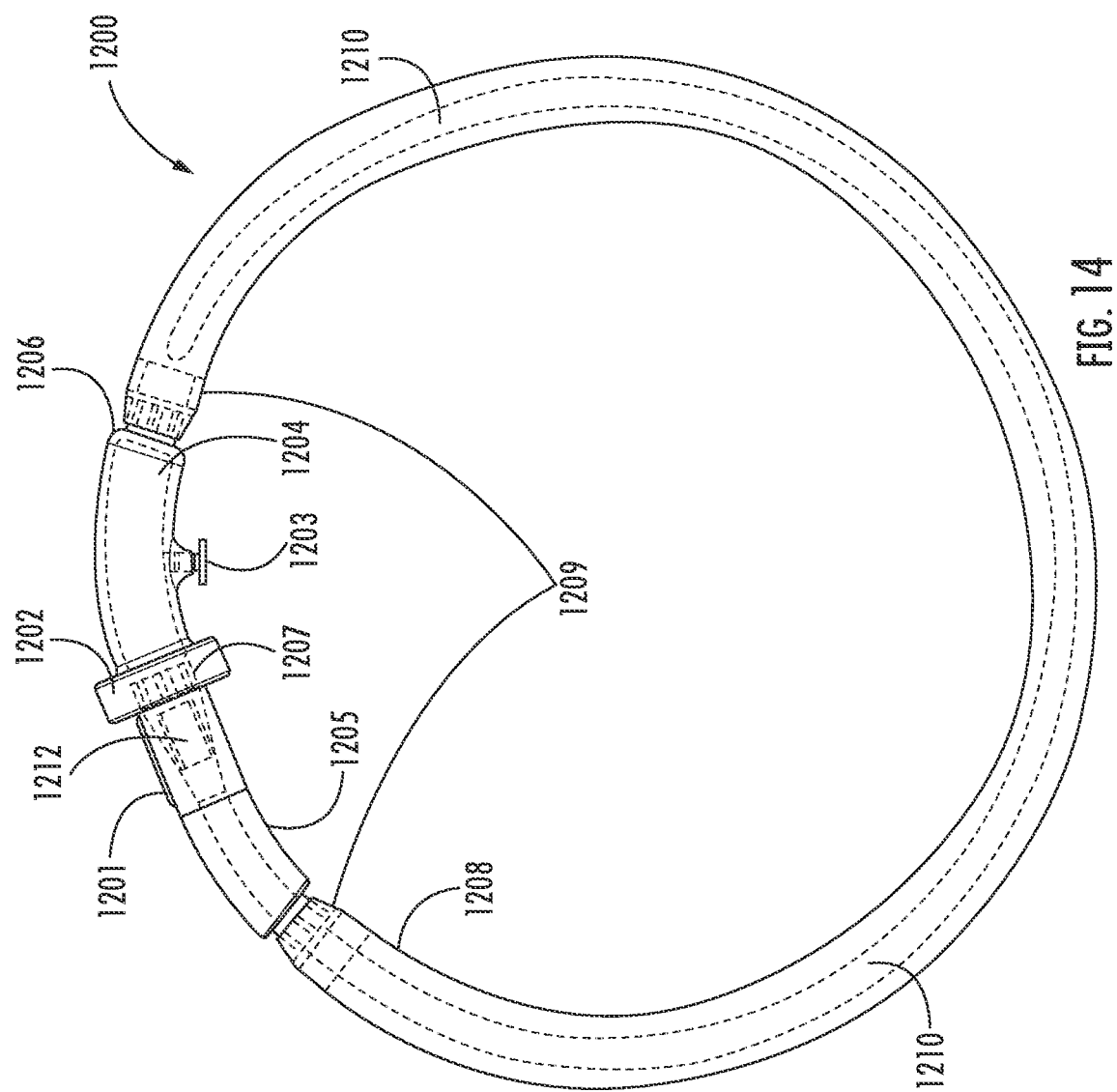
FIG. 14 is a side view of an illustrative embodiment of an RFID-tagged medical device specially adapted for use by females for the purposes of urinary catheterization.

In accordance with other aspects of the present invention, an individual catheterization system may include an at-home sterilization and data acquisition and deposition device 1000 with an RFID scanner 1004 configured into the housing 1020 of said device 1000, a software-enabled analysis of data acquired through the system, a set of accessories to enable to proper lubrication, cleaning, and radiation-based sterilization of medical devices, and a set of RFID-enabled medical devices 1100, 1200 designed to facilitate sterile emptying of the bladder by providing a tactile interface 1102, 1202 that prevents direct contact between the individual and the parts of the medical devices that enter the individual's body as illustrated in FIGS. 13 and 14.

In accordance with other aspects of the present invention, the set of accessories to enable proper lubrication, cleaning, and radiation-based sterilization of medical devices 1100, 1200 may include a lubricant bottle that is specially adapted to mate with a port 1103, 1203 located on, and deposit lubricant without leaking into, a lubricant reservoir 1104, 1204 that subsequently applies lubricant to the exterior surface of the portions of the RFID-enabled medical devices 1100, 1200 that enter the body. The lubricant dispensed by the lubricant bottle may be further comprised of or be mixed with a pharmaceutical agent intended for reducing active pathogens post-sterilization (e.g., the device includes the ability to disperse pharmaceuticals on catheter as it lubricates). Alternatively, the pharmaceutical agent may be intended to counteract inflammation.

In accordance with other aspects of the present invention, the set of accessories to enable proper lubrication, cleaning, and radiation-based sterilization of medical devices 1100, 1200 may include a elongate silicone brush capable of dispersing chemical sterilizing agents in powder, gel, or liquid form while also abrading pathogenic residue and/or biofilms from the interior surface of an elongate, tubular medical device without causing damage to the interior surface of the elongate, tubular medical device.

In accordance with other aspects of the present invention, the RFID-enabled medical devices 1100, 1200 may be comprised of a set of mating stiff and flexible components that detach for easy cleaning, which are further comprised of components that intended for use outside of and inside of the body. These devices 1100, 1200 may include curved funnels 1105, 1205 at their distal end to facilitate the flow of liquid throughout the devices 1100, 1200 while minimizing the splashing of liquid. These devices 1100, 1200 may include stiff insertion aids 1106, 1206 that are adapted to male and female anatomy to provide structure and support during the insertion of flexible urinary catheters, and which further provide a means of sterile lubrication, alignment, and insertion of urinary catheters into the urethral tract. These devices 1100, 1200 may include components that allow the devices to self-seal through the implementation of a quarter-turn luer lock or some other substantially sealing and mating mechanisms 1107, 1207 in the distal funnel 1105, 1205 and proximal insertion aid 1106, 1206 ends of these devices 1100, 1200, in order to allow individuals to carry these devices 1100, 1200 in transit without fear of leakage from the devices 1100, 1200 once they have been used.

The insertion aids 1106, 1206 may be further comprised of flexible bags 1108, 1208 that mate to both the catheter and the stiff components of the insertion aids via stiff collars 1109, 1209, therein providing a protective yet tactile barrier that allow individuals to directly manipulate the flexible catheters without contaminating them with pathogens. These devices 1100, 1200 may be made from materials with a high degree of sterilization radiation transparency such as polypropylene film. These devices 1100, 1200 may be engineered with additional reinforcing material in structurally vulnerable areas such as eyelets and joins in order to maximize their lifespan over a pre-specified period of use. These devices 1100, 1200 may be so engineered in order to be successfully reused and sterilized in the at-home sterilization device 1000 fifty to one hundred times each. These devices 1100, 1200 may be designed to maximize usability by individuals with limited dexterity through the incorporation of oversize tabs and other accessible features through their design.

In accordance with yet other aspects of the present invention, the individual catheterization system may include an electronic medical record or medical device distribution data interface that utilizes data gathered from the RFID scanner 1004 within the sterilization and data acquisition and deposition device 1000 in a HIPAA compliant manner and securely transmits it to various stakeholders in the healthcare ecosystem, including, but not limited to, urologists, occupational therapists, physical therapists, and medical device distributors. This data interface may further be comprised of an anonymization and aggregation of the data gathered from all deployed sterilization and data acquisition and deposition devices in order to analyze trends and correlations of catheterization practices and urinary tract infection incidence, and may further communicate to the user of such devices best practices for catheterization in order to avoid infections.

Specifically, the medical device 1100, 1200 may include or be a catheter. According to aspects of this invention, the catheter 1100, 1200 may be a urinary intermittent catheter, primarily fabricated from a UVC-transparent and flexible material with a stiff funnel 1105, 1205 fabricated from cyclic olefin copolymer or FEP, and intended to be inserted into the human body for 3-5 minutes at a time to facilitate the drainage of urine from the bladder into a receptacle. For males, the catheter 1100, 1200 may likely be between 11.5 and 12 inches long (not including the funnel, which is itself 1 inch long); for females, the catheter 1100, 1200 may likely be between 3 and 5 inches long (not including the funnel).

The catheter 1100, 1200 is tagged with an RFID chip 1101, 1201 that is scanned upon placement into the sterilizer 1000. The chip 1101, 1201 may contain authentication information [e.g. serial number] as well as usage information [how many times that specific catheter 1100, 1200 has been sterilized]. This information could potentially grow to include time and date of the last sterilization. This RFID tag might actually go on the insertion aid 1106, 1206 instead of on the catheter 1100, 1200 directly. The electronics suite of the catheter 1100, 1200 may grow over time to give the catheter 1100, 1200 the capability to perform real-time analysis of the bioburden present within the urine. Each of the electronic sensors used to perform this analysis would potentially store their readings in a separate RFID chip 1101, 1201 [e.g. an RFID array] or a single high-capacity RFID chip. The RFID tag present on the catheter 1100, 1200 may also be scannable by mobile app and mobile phone RFID reader to validate the number of uses left in the catheter 1100, 1200 or insertion aid 1106, 1206 and generally access the data remotely/in the absence of the sterilizer 1000.

The catheter 1100, 1200 may include many features related to reusability. For example, the catheter may include reinforced eyelets, such that the catheter 1100, 1200 may be reinforced with additional material around the drainage eyelets in order to withstand material fatigue over time. In another example, the catheter 1100, 1200 may include a reinforced mating area with the funnel 1105, 1205. The catheter 1100, 1200 may be reinforced with additional material around where it mates with a hard funnel 1105, 1205 to facilitate drainage of urine away from the body, in order to withstand material fatigue over time. The catheter 1100, 1200 may also be UVC transparent, such that all parts of the catheter 1100, 1200 may be made with UVC transparent materials that allow germicidal wavelengths of UV light to simultaneously sterilize the interior and exterior surfaces of the catheter 1100, 1200. The catheter 1100, 1200 may have a usage lifetime of as much as 100 uses each.

The funnel 1105, 1205 of the catheter 1100, 1200 may also include various features. For example, the catheter 1100, 1200 may include a curved funnel 1105, 1205 that reduces material strain on the catheter 1100, 1200 when stored in conjunction with the insertion aid 1106, 1206 and reduces the flow rate of urine exiting the funnel 1105, 1205 end of the catheter 1100, 1200 by virtue of increasing surface area contact between the funnel 1105, 1205 walls and the urine. Additionally, the distal end of the catheter funnel 1105, 1205 may include a quarter turn female luer lock component that mates with the proximal end of insertion aid 1106, 1206. This provides a substantially water-tight, air-tight seal. Additionally, this component can interface with a number of catheter product accessories such as a portable urine drainage bag or an adaptor that facilitates connection to a standard water bottle. The seal is substantially air- and water-tight, enabling a hermetic seal that allows for sterile transport of the insertion aid 1106, 1206 and the catheter 1100, 1200 once fully assembled.

Additionally, the proximal end of the catheter funnel 1105, 1205 may include a female mating interface that either accepts a snap fit or threaded male insert from the insertion aid 1106, 1206. This enables the insertion aid 1106, 1206 and the catheter 1100, 1200 to be disassembled for rinsing and cleaning. The seal is substantially air- and water-tight, enabling a hermetic seal that allows for sterile transport of the insertion aid 1106, 1206 and the catheter 1100, 1200 once fully assembled.

In another embodiment, the catheter 1100, 1200 may be include increased usability by people with limited dexterity. These catheter 1100, 1200 may include easy-to-grip plastic tabs and/or loops around each distinct component of the catheter 1100, 1200 such that a single finger can be used to disassemble or assemble the catheter 1100, 1200 and insertion aid 1106, 1206. Additionally, the catheter 1100, 1200 may be made out of biodegradable/compostable plastics.

The medical device and catheter 1100, 1200 may include an insertion aid 1106, 1206 as illustrated in FIGS. 13 and 14. The insertion aid 1106, 1206 may include a stiff apparatus that mates with a flexible, thin plastic bag with threaded or snap fit collars. The stiff apparatus provides support and lubrication to the catheter 1100, 1200 as it is being inserted into the body, while the flexible, thin plastic bag acts as a prophylactic barrier between the catheter 1100, 1200 and the human body, to reduce contact contamination risk at the moment of insertion into the body.

The insertion aid 1106, 1206 may include an insertion tip. The proximal end of the insertion aid 1106, 1206 may include a flexible insertion tip whose inner diameter matches the French size of the catheter 1100, 1200, with a thickness between 5 and 10 mils [thousandths of an inch]. The tip acts as a prophylactic barrier between the catheter 1100, 1200 and the meatus of the urethral opening. The insertion aid 1106, 1206 may also include an usability handle. For example, the male version of the insertion aid 1106, 1206 features a usability handle that can be used to support the insertion aid 1106, 1206 against the shaft of the penis throughout insertion. The usability handle may be designed so that one hand is sufficient to stabilize the insertion aid 1106, 1206 and catheter 1100, 1200 while the other hand is used to insert the catheter 1100, 1200 into the body.

The insertion aid 1106, 1206 may include an usability flange. The female version of the insertion aid 1106, 1206 may include a flange at the base of the insertion tip that female users can apply pressure to with their fingers to hold the insertion aid 1106, 1206 securely against the urethral opening. The flange has been designed to be compatible with the anatomical geometry of the vagina, and can be used to securely hold the insertion aid 1106, 1206 against the urethral opening while simultaneously spreading the labia apart for easier insertion of the catheter 1100, 1200.

The insertion aid 1106, 1206 may include a lubrication reservoir that can hold a predetermined amount of lubricant without leakage. For example, as the catheter 1100, 1200 is inserted into the body and travels through the reservoir and the insertion tip, the catheter 1100, 1200 is coated with a thin layer of lubricant to facilitate insertion. The lubrication reservoir may be filled through a luer lock mating system, wherein the lubrication reservoir has a sealed female port that mates with a male applicator tip that screws onto a refillable lubrication bottle.

The insertion aid 1106, 1206 may also include a stiff insertion aid proximal interface that is located at the proximal end of the stiff insertion aid component and features a quarter turn male luer lock component that mates with the proximal end of catheter 1100, 1200. The seal is substantially air- and water-tight, enabling a hermetic seal that allows for sterile transport of the insertion aid 1106, 1206 and catheter 1100, 1200 once fully assembled. Additionally, the insertion aid 1106, 1206 may include a stiff insertion aid distal interface that is located at the distal end of the stiff insertion aid component and features a female mating interface that either accepts a snap fit or threaded male insert from the insertion aid bag. This enables the insertion aid 1106, 1206 and catheter 1100, 1200 to be disassembled for rinsing and cleaning. The seal is substantially air- and water-tight, enabling a hermetic seal that allows for sterile transport of the insertion aid 1106, 1206 and catheter 1100, 1200 once fully assembled.

The insertion aid 1106, 1206 may also include a collared bag. A flexible component of the insertion aid 1106, 1206 may be comprised of a flexible plastic bag that is bookended by collars that are either threaded or have a snap fit feature on them to facilitate mating with and subsequent disassembly from the insertion aid 1106, 1206 and catheter 1100, 1200.

Additionally, the insertion aid 1106, 1206 may include increased usability by people with limited dexterity. For example, this increased usability may include easy-to-grip plastic tabs and/or loops around each distinct component of the insertion aid such that a single finger can be used to disassemble or assemble the catheter 1100, 1200 and insertion aid 1106, 1206.

The insertion aid 1106, 1206 may be RFID tagged with an RFID chip 1101, 1201 that is scanned upon placement into the sterilizer 1000. The chip 1101, 1201 may contain authentication information [e.g. serial number] as well as usage information [how many times that specific catheter has been sterilized]. This information could potentially grow to include time and date of the last sterilization. This RFID tag might actually go on the insertion aid 1106, 1206 instead of on the catheter 1100, 1200 directly. The electronics suite of the insertion aid 1106, 1206 may include the insertion aid 1106, 1206 with the capability to perform real-time analysis of the bioburden present within the urine. Each of the electronic sensors used to perform this analysis would potentially store their readings in a separate RFID chip [e.g. an RFID array] or a single high-capacity RFID chip.

The RFID tag present on the insertion aid 1106, 1206 may also be scannable by mobile app and mobile phone RFID reader to validate the number of uses left in the catheter 1100, 1200 or the insertion aid 1106, 1206 and generally access the data remotely/in the absence of the sterilizer 1000.

All parts of the insertion aid 1106, 1206 may be made with UVC transparent materials that allow germicidal wavelengths of UV light to simultaneously sterilize the interior and exterior surfaces of the insertion aid. The insertion aid 1106, 1206 may have a usage lifetime of 100 uses each.

The sterilizer 1000 may include a sterilizer interface. The sterilizer interface may provide a color-coded display for remaining uses. The sterilizer 1000 may inform the user how many uses is left in each catheter 1100, 1200 based on their relative position within the sterilizer 1000. For example, the status indicator may shine green if the catheter 1100, 1200 or insertion aid 1106, 1206 has been used less than 75 times each; yellow if the catheter 1100, 1200 or insertion aid 1106, 1206 has been used between 75 and 95 times; and red if the catheter 1100, 1200 or insertion aid 1106, 1206 has been used between 95 and 100 times. Other colors and usage times may be utilized without departing from this invention. The sterilizer 1000 may include an LED pixel matrix that visually indicates to the user how much time is left in the sterilization cycle.

The sterilizer 1000 may include various software features. The sterilizer 1000 may include an automated replenishment. For example, based on number of uses remaining in the plurality of catheters 1100, 1200 and insertion aids 1106, 1206 used with the sterilizer 1000, the system can automatically initiate a catheter reorder with the user's medical device distributor. In another embodiment, the sterilizer 1000 may include catheterization analysis. For example, the software may analyze the frequency of catheterization based on detection of catheter removal from the sterilizer [RFID reader scans the sterilizer interior every time the door 1006 is opened or closed] and frequency of sterilization cycles. In another embodiment, the sterilizer 1000 may include application pairing, where the sterilizer 1000 may pair with a digital application on a mobile device to provide more detailed status updates and diagnostics of the device 1000 to the user. The sterilizer may use data gathered from the application [UTI incidence, urologist check-ups, etc.] to augment its analysis of the user's catheterization data. In another embodiment, the sterilizer 1000 may include EHR integration to provide urologists with seamless, real-time updates on catheterization frequency and sterilizer analysis.

The sterilizer 1000 may also include portable, battery-powered sterilizer 1000 that primarily utilizes UVC LEDs to sterilize used catheters 1100, 1200 between uses. This portable sterilizer 1000 would likely have a carrying capacity of one catheter 1100, 1200 and insertion aid 1106, 1206 at a time.

According to another embodiment, a catheter scrubber may be utilized. The scrubber may be a 12-inch-long silicone brush that can scrub the interior of a catheter 1100, 1200 without materially damaging the catheter 1100, 1200 itself. The scrubber may be used to reduce biofilm/pathogenic residue on the inside surface of the catheter 1100, 1200. The scrubber may be coated or coatable with an additional disinfecting agent [powder or liquid].

The sterilizer 1000 may include a digital application for use with a mobile device. The digital application may be a companion application for the sterilizer 1000 that features added functionality for the user. For example, the digital application may provide on-the-go validation and usage information, such that the application can scan each catheter 1100, 1200 and insertion aid 1106, 1206 using the RFID/NFC technology in most mobile phones to validate authenticity and tell individuals how many uses they have left. In another embodiment, the digital application may include replenishment reminders and confirmation, such that the application can insert reminders in their calendar to re-order catheters from their distributor and update these reminders based on real-time usage of catheters. The application can additionally notify users of automated replenishment orders and ask for their consent before submitting the order for fulfillment. In another embodiment, the digital application may include location-based data gathering, such that using the application with location services enabled allows the application to ask individuals contextual questions. For example, if located near a hospital, the application may ask the user if they are experiencing UTI-like symptoms. Similar survey questions may be sent out periodically in the absence of location services to gather UTI-incidence data for analysis of catheterization habits and UTI incidence. The digital application may utilize anonymized data gathered across all users of the system and the application may suggest behavioral changes to limit UTI incidence.

Figure 15:
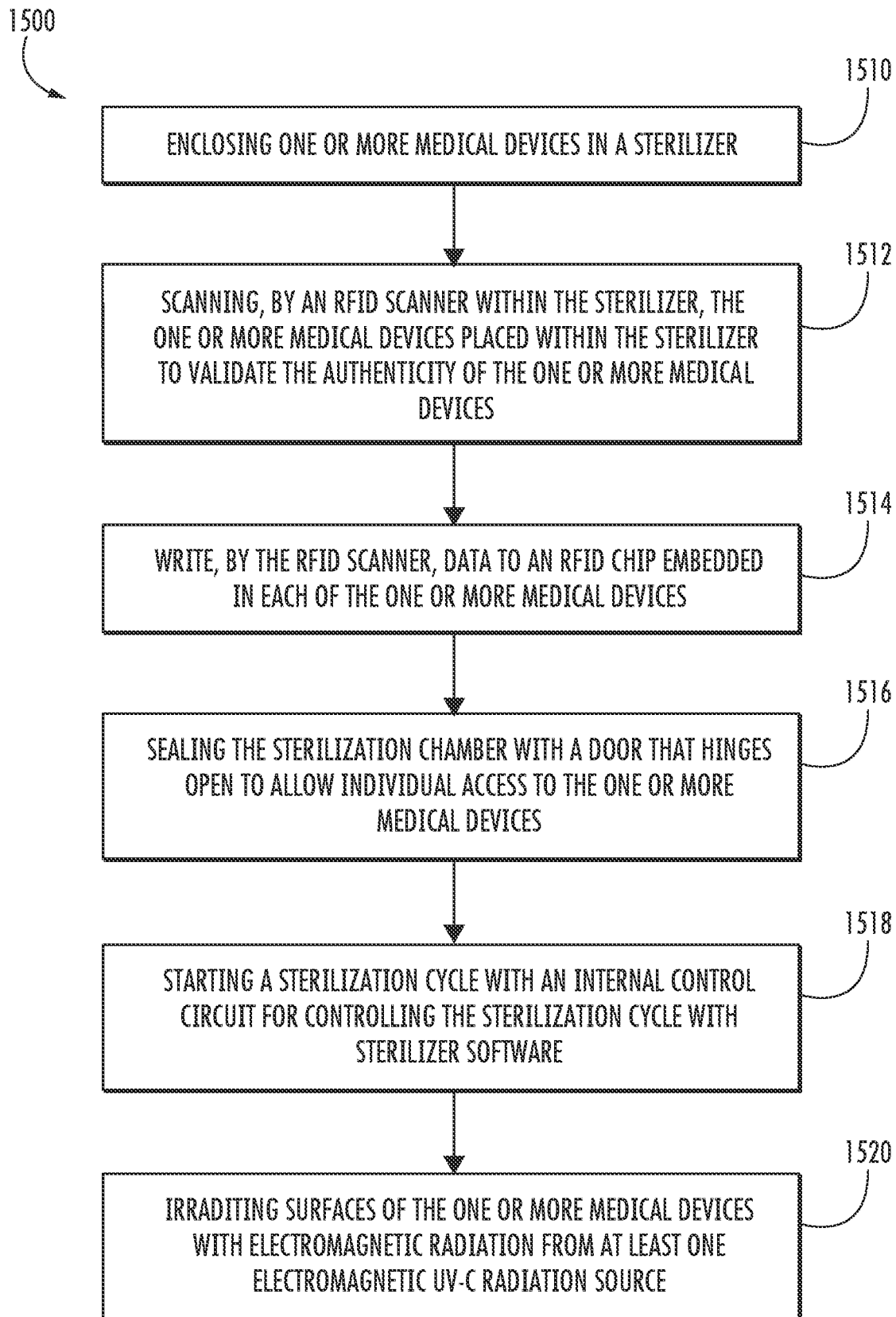
FIG. 15 is a flowchart for a method for sterilizing one or more medical devices using electromagnetic radiation according to aspects of this invention.

In another embodiment, as illustrated in FIG. 15, a method 1500 for sterilizing one or more medical devices using electromagnetic radiation may include the steps of: enclosing one or more medical devices in a sterilizer 1510; scanning, by an RFID scanner within the sterilizer, the one or more medical devices placed within the sterilizer to validate the authenticity of the one or more medical devices 1512; write, by the RFID scanner, data to an RFID chip embedded in each of the one or more medical devices 1514; sealing the sterilization chamber with a door that hinges open to allow individual access to the one or more medical devices 1516; starting a sterilization cycle with an internal control circuit for controlling the sterilization cycle with sterilizer software 1518; and irradiating surfaces of the one or more medical devices with electromagnetic radiation from at least one electromagnetic UV-C radiation source 1520.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying Claims.

We claim:

1. A reusable urinary catheter product, comprising:
   a container comprising a housing and a re-closable lid, the housing having a first compartment defining a sterilization chamber and a second compartment defining an interior, the first compartment and second compartment being separated by one or more walls that allow the passage of a sterilization and disinfecting media;
   a urinary catheter located in the first compartment;
   a fluid adapted to enhance sterilizing of the urinary catheter, wherein the fluid contains one or more of the following: water, hydrogen peroxide, or silver particles; and
   a sterilization and disinfection source located in the second compartment, wherein the sterilization and disinfecting media emitted from the sterilization and disinfection source passes through the one or more walls and into the first compartment.

2. The reusable urinary catheter product of claim 1, wherein the one or more walls includes a UV transparent optical window.

3. The reusable urinary catheter product of claim 1, wherein the sterilizing light source comprises one or more light emitting diodes.

4. The reusable urinary catheter product of claim 3, wherein the one or more light emitting diodes are embedded within the one or more walls.

5. The reusable urinary catheter product of claim 1 further comprising:
a power source for powering the sterilizing light source.

6. The reusable urinary catheter product of claim 1, wherein the sterilizing chamber further includes reflective material that reflects the sterilizing light.

7. The reusable urinary catheter product of claim 1, wherein the sterilizing light source is a UV light source.

8. A reusable urinary catheter kit, comprising:
a housing including
  a first member defined by one or more walls defining an interior,
  a second member defining a lid,
  and
  a sterilization chamber defined by the interior and the lid, with the interior defining an access opening of the sterilization chamber;
a fluidics system connected to the sterilization chamber and configured to circulate a fluid through the sterilization chamber when the second member is in the closed condition; and
a reusable urinary catheter at least partially positioned within the sterilization chamber, wherein the second member is adjustably associated to the first member and configured to move between a closed condition in which the lid overlays the access opening to enclose the reusable urinary catheter within the chamber and an open condition in which the lid is spaced from the access opening.

9. The reusable urinary catheter kit of claim 8, wherein the housing defines a closed loop when the second member is in the closed condition.

10. The reusable urinary catheter kit of claim 8, wherein the sterilization chamber is fluid-tight when the second member is in the closed condition.

11. The reusable urinary catheter kit of claim 8, wherein the fluid is adapted to enhance sterilizing of the reusable urinary catheter.

12. The reusable urinary catheter kit of claim 8, wherein the fluid contains one or more of the following: water, hydrogen peroxide, or silver particles.

13. The reusable urinary catheter kit of claim 8 further comprising:
at least one light source associated with the sterilization chamber and configured to irradiate at least a portion of the reusable urinary catheter with sterilizing light.

14. A reusable urinary catheter product, comprising:
a housing comprising a distal section, a proximal section, and a middle section therebetween, wherein the housing includes one or more walls defining an interior and a sterilization chamber defined by the interior and a lid;
a sterilizing and lubricating fluid within the interior, the sterilizing and lubricating fluid comprising a sterilizing medium, wherein the sterilizing and lubricating fluid contains one or more of the following: water, hydrogen peroxide, or silver particles; and
a reusable catheter including a catheter shaft having a distal end portion and a proximal end portion, the catheter shaft being located within the sterilization chamber, the catheter shaft including a coating thereon, wherein the sterilizing and lubricating fluid hydrates the coating and sterilizes the catheter, the catheter being configured to repeatedly inserted into and removed from the housing.

15. The reusable urinary catheter product of claim 14, wherein the housing further comprises a textured grip to provide an ergonomic handle.

16. The reusable urinary catheter product of claim 14 further comprising:
a micro fluid pump to pump the sterilizing and lubricating fluid into and out of the sterilization chamber.

17. The reusable urinary catheter product of claim 14 further comprising:
at least one light source associated with the sterilization chamber and configured to irradiate at least a portion of the reusable catheter with sterilizing light.

* * * * *